United States Patent [19]

Hammer et al.

[11] Patent Number: 5,637,601
[45] Date of Patent: Jun. 10, 1997

[54] ANTICHOLINERGIC COMPOUNDS, COMPOSITIONS AND METHODS OF TREATMENT

[75] Inventors: Richard H. Hammer; Nicholas S. Bodor, both of Gainesville, Fla.

[73] Assignee: University of Florida, Gainesville, Fla.

[21] Appl. No.: 453,450

[22] Filed: May 30, 1995

Related U.S. Application Data

[62] Division of Ser. No. 366,464, Dec. 30, 1994, which is a division of Ser. No. 104,650, Aug. 11, 1993, Pat. No. 5,418,244, which is a division of Ser. No. 931,320, Aug. 18, 1992, Pat. No. 5,258,388, which is a division of Ser. No. 558,823, Jul. 27, 1990, Pat. No. 5,223,528, which is a continuation of Ser. No. 245,333, Sep. 16, 1988, abandoned, which is a continuation-in-part of Ser. No. 189,709, May 3, 1988, abandoned, which is a continuation-in-part of Ser. No. 130,454, Nov. 17, 1987, abandoned, which is a continuation of PCT/US87/00533, Mar. 17, 1987, which is a continuation-in-part of Ser. No. 839,941, Mar. 17, 1986, abandoned.

[51] Int. Cl.$^6$ ............ A61K 31/445; C07D 211/40
[52] U.S. Cl. ............ 514/327; 514/329; 546/221; 546/222; 546/224; 546/216
[58] Field of Search ............ 514/327, 329; 546/222, 221, 224, 216

[56] References Cited

U.S. PATENT DOCUMENTS

| | | | |
|---|---|---|---|
| 2,774,767 | 12/1956 | Ehrhart et al. | 260/295 |
| 2,814,623 | 11/1957 | Moffett | 546/91 |
| 3,312,709 | 4/1967 | MacMillan | 560/110 |
| 3,557,125 | 1/1971 | Zeile et al. | 546/130 |
| 3,649,630 | 3/1972 | Meunier et al. | 546/91 |
| 4,160,099 | 7/1979 | Bodor | 546/91 |
| 4,479,932 | 10/1984 | Bodor | 564/381 |
| 4,771,059 | 9/1988 | Bodor | 514/355 |
| 4,916,145 | 4/1990 | Tilley et al. | 514/357 |
| 5,208,247 | 5/1993 | Trova et al. | 514/358 |
| 5,216,170 | 6/1993 | Lindel et al. | 546/300 |
| 5,223,528 | 6/1993 | Hammer et al. | 514/412 |
| 5,258,388 | 11/1993 | Hammer et al. | 514/291 |
| 5,418,244 | 5/1995 | Hammer et al. | 514/357 |

FOREIGN PATENT DOCUMENTS

| | | |
|---|---|---|
| 198432 | 7/1958 | Austria. |
| 6937M | 5/1969 | France. |
| 871948 | 10/1987 | South Africa. |
| 833008 | 4/1960 | United Kingdom. |

OTHER PUBLICATIONS

Bodor et al, *J. Med. Chem.*, 1980, 23, 474–480.
Bodor, *Advances in Drug Research*, vol. 13, 255–331 (1984).
Hammer et al, *Drug Design and Delivery*, 1988, vol. 2, 207–219.
Bodor et al, *Journal of Biopharmaceutical Sciences*, 1(3), 215–223 (1990).
Hammer et al, *Current Eye Research*, vol. 10, No. 6, 565–570 (1991).
Hammer et al, *Drug Design and Delivery*, vol. 2, 207–219 (1988).
Bodor, in *Advances in Drug Research*, ed. Bernard Testa, vol. 13, Academic Press, London, 1984, 256–263, 311–312, 322–323.
Notari, in *Design of Biopharmaceutical Properties through Prodrugs and Analogs*, ed. Edward B. Roche, American Pharmaceutical Association Academy of Pharmaceutical Sciences, Washington, D.C., 1977, 68–69, 78–79.
Bodor, in *Design of Prodrugs*, ed. H. Bundgaard, Elsevier Science Publishers B.V., Amsterdam, 1985, 333–353.
Bundgaard, in *Design of Prodrugs*, ed. H. Bundgaard, Elsevier Science Publishers B.V., Amsterdam, 1985, v–vii.
Bundgaard, in *Design of Prodrugs*, ed. H. Bundgaard, Elsevier Science Publishers B.V., Amsterdam, 1985, 1–4.
Hadgraft, in *Design of Prodrugs*, ed. H. Bundgaard, Elsevier Science Publishers B.V., Amsterdam, 1985, 271–289.
Harper, in *Absorption and Distribution of Drugs*, ed. T.B. Binns, The Williams and Wilkins Company, Baltimore, MD, 1964, 103–108.
*The Pharmacological Basis of Therapeutics*, fifth edition, eds. L.S. Goodman and A. Gilman, MacMillan Publishing Co., Inc., New York, 1975, 515–516.
MacMillan et al, *J. Investigative Dermatology*, 43, 363, 371–377 (1964).
*Cutting's Handbook of Pharmacology*, Seventh edition, ed. T.Z. Csáky et al, Appleton–Century–Crofts, Norwalk, Connecticut, 1984, 622–638.
*Chemical Abstracts* 63: 13137g, 1965.
*Chemical Abstracts* 63: 13137f, 1965.
*Chemical Abstracts* 62: 2736b, 1965.
*Chemical Abstracts* 62: 469g, 1965.
*Chemical Abstracts* 55: 581g, 1961.
Salmon–Legagneur et al, *Bull. Soc. Chim. France* 8, 2270–2275 (1965).
Kulp et al, *J. Med. Chem.* 7(6), 831 (1964).
Diaz Gomez et al, *Biochemical Pharmacology*, vol. 20, pp. 929–942 (1971).
*Chemical Abstracts* 57, 8541d–8542b (1962), Buttini et al.

*Primary Examiner*—Shailendra Kumar
*Attorney, Agent, or Firm*—Burns, Doane, Swecker & Mathis

[57] ABSTRACT

Compounds of the formula

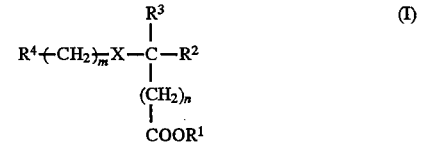

wherein the variables are defined in the specification; and acid addition and quaternary ammonium salts of formula (I) compounds are described. The compounds and their salts are soft anticholinergic/antisecretory agents especially useful as mydriatics and as antiperspirants.

23 Claims, 1 Drawing Sheet

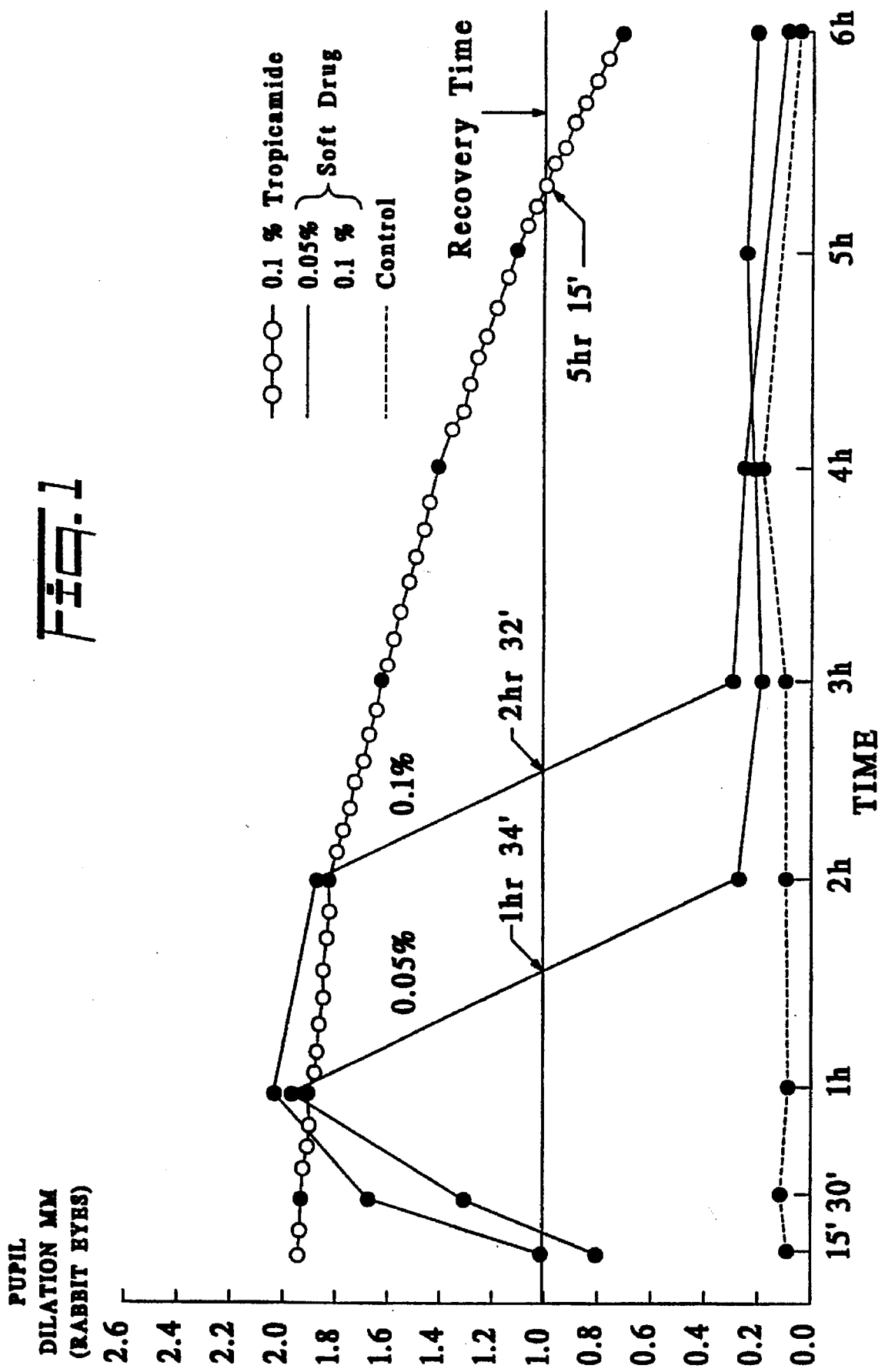

ANTICHOLINERGIC COMPOUNDS, COMPOSITIONS AND METHODS OF TREATMENT

CROSS-REFERENCE TO RELATED APPLICATIONS

This application is a divisional of application Ser. No. 08/366,464, filed Dec. 30, 1994, which is a divisional of Ser. No. 08/104,650, filed Aug. 11, 1993, now U.S. Pat. No. 5,418,244, which is a divisional of application Ser. No. 07/931,320, filed Aug. 18, 1992, now U.S. Pat. No. 5,258,388, which is a divisional of application Ser. No. 07/558,823, filed Jul. 27, 1990, now U.S. Pat. No. 5,223,528, which is a continuation of application Ser. No. 07/245,333, filed Sep. 16, 1988, now abandoned, which is a continuation-in-part of application Ser. No. 07/189,709, filed May 3, 1988, now abandoned, which is a continuation-in-part of application Ser. No. 07/130,454, filed Nov. 17, 1987, now abandoned, which is the U.S. national phase of PCT/US87/00533, filed Mar. 17, 1987 and a continuation-in-part of application Ser. No. 06/839,941, filed Mar. 17, 1986, now abandoned.

BACKGROUND OF THE INVENTION

1. Field of the Invention

The present invention relates to certain novel anticholinergic, mydriatic and antisecretory compounds as well as pharmaceutical and antiperspirant compositions containing the novel compounds and methods of treatment of animals and humans in need thereof.

2. Prior Art

Commercially available anticholinergic drugs such as atropine and scopolamine and their synthetic analogs all share a variety of undesirable side effects. In the elderly, excitement, agitation and drowsiness are frequently observed even in small doses. Dangerous central nervous system mediated psychotic reactions and behavioral disturbances have occurred in children after topical ocular administration. Ophthalmic use may also induce local side effects such as transient stinging, allergic lid reactions, follicular conjunctivitis, edema and photophobia. See *Toxicology of Commercial Products*, R. E. Gosselin et al, Eds. (Williams & Wilkins, Balt., 4th Ed., 1976) Sec. III, pp. 43–46.

Mydriatic agents are an important class of compounds that are used to dilate the pupil. Mydriasis is required during ophthalmic examinations, in order to provide for a more complete examination of the fundus, the vitreous and the periphery of the lens, and in various surgical procedures such as those reported by Freeman et al, *American Intra-Ocular Society Journal* 7:172–173 (1981) (e.g., vitrectomy, lens extraction, and intraocular lens implantation). Commercially available mydriatic drugs such as atropine, scopolamine, homatropine and their synthetic analogs all suffer from several disadvantages. Because the mydriasis induced by these agents causes blurred vision and is of a relatively long duration, i.e., several hours, it is necessary to virtually immobilize the patient after the ophthalmic examination until the mydriasis subsides and the patient can resume normal activities. Ophthalmic use of these agents may also induce local side effects such as transient stinging, allergic lid reactions, follicular conjunctivitis, edema and photophobia. See R. E. Gosselin et al supra.

One of the commonly known effects of antisecretory agents is inhibition of eccrine sweating and compensatory cutaneous flush. Systemically administered anticholinergics do generally decrease the secretion of the sweat glands, as well as saliva and that of other secretory glands. Based on these properties, it has been long investigated how one could safely use an antimuscarinic agent to inhibit local hyperhydration by topical application. Although a wide range of compounds have proved to be highly effective as antiperspirants when applied topically, it was concluded that they are in general not safe to use because of the well-known systemic effects of these drugs at a possible over-exposure. Side effects appear even at very low concentrations when highly potent anticholinergics are used.

It would be desirable to obtain practically exclusively locally acting agents, which is possible if the rate of penetration-absorption and the rate of in vivo destruction are well-balanced: if the latter is faster, no buildup and consequently no systemic effects due to the drug would be observed.

New drug design approaches can lead to novel, safer anticholinergic drugs with fewer side effects. One new approach that has shown promise is the soft drug design proposed by Bodor (Bodor, *Chemtech*, Jan. 28, 1984, pp. 28–38, and Bodor, in *Design of Biopharmaceutical Properties Through Prodrugs and Analogs*, ed. E. B. Roche, Washington, D.C., Academy of Pharmaceutical Sciences, 1977, pp. 98–135) and used to design and synthesize anticholinergic agents and other pharmacologically active classes of drugs. Previous soft ester analogs of anticholinergics were synthesized from cyclopentylphenylacetic acid, phenylacetic acid and branched aliphatic carboxylic acids. These soft drugs, also known as soft analogs, are described in U.K. Patent Application No. 7848850, filed Dec. 18, 1978 and published under U.K. Patent Application Publication No. 2010270A on Jun. 27, 1979, and in a related publication by Bodor et al, *J. Med. Chem.* 23, pp. 474–480 (1980). Nevertheless, it would be desirable to design yet other soft anticholinergic drugs, especially to design such drugs using the "inactive metabolite approach". According to this approach, an inactive metabolite (which could be hypothetical) is selected and reactivated by synthesizing an agent resembling the parent drug. The soft drug is designed with a molecular soft spot which should predictably metabolize back to the inactive starting metabolite in vivo in one step and without going through toxic intermediates.

It is an object of the present invention to provide such novel anticholinergic compounds which exhibit anticholinergic properties, which induce mydriasis and which also exhibit local antisecretory, especially antiperspirant, properties as well as pharmaceutical and antiperspirant compositions and methods of treatment embodying those compounds which are more effective and less toxic than those presently available.

SUMMARY OF THE INVENTION

The foregoing and other objects are realized by the present invention which provides novel compounds having the formula:

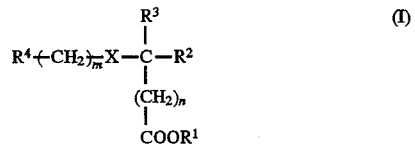

wherein:

$R^1$ is $C_1$–$C_8$ straight or branched alkyl; $C_2$–$C_8$ straight or branched alkenyl; ($C_3$–$C_8$ cycloalkyl)-$C_pH_{2p}$— wherein p is an integer from 0 to 4, and wherein the 3- to 8-membered ring portion may optionally bear 1 to 4 $C_1$–$C_4$ straight or branched alkyl substituents; ($C_3$–$C_8$ cycloalkenyl)-$C_pH_{2p}$— wherein p is an integer from 0 to 4 and wherein the 3- to 8-membered ring portion may optionally bear 1 to 4 $C_1$–$C_4$ straight or branched alkyl substituents; $C_6H_5$—$C_qH_{2q}$— wherein q is an integer from 1 to 4; or ($C_6$–$C_{18}$ polycarbocyclic)-$C_pH_{2p}$— wherein p is an integer from 0 to 4, the 6- to 18-membered ring portion consisting of 2 to 4 rings which may be bridged or fused, which may be saturated or unsaturated and which may optionally bear one or more $C_1$–$C_8$ straight or branched alkyl substituents, the total carbon atom content of all such optional alkyl substituents being from 1 to 10;

$R^2$ is any radical defined by $R^1$ above, or $R^2$ is phenyl optionally bearing 1 to 3 $C_1$–$C_4$ straight or branched alkyl substituents;

$R^3$ is H, 2-, 3- or 4-pyridyl, phenyl optionally bearing 1 to 3 $C_1$–$C_4$ straight or branched alkyl substituents, $C_1$–$C_8$ straight or branched alkyl or ($C_3$–$C_8$ cycloalkyl)-$C_pH_{2p}$— wherein p is an integer from 0 to 4 and wherein the 3- to 8-membered ring portion may optionally bear 1 to 4 $C_1$–$C_4$ straight or branched alkyl substituents;

n is an integer from 0 to 4;

X is

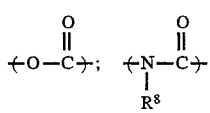

wherein $R^8$ is H or $C_1$–$C_5$ straight or branched alkyl;

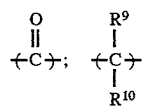

wherein each of $R^9$ and $9^{10}$, which may be the same or different, is H or $C_1$–$C_5$ straight or branched alkyl; –[S(CH$_2$)$_x$–]–wherein x is 0 or 1; –[O(CH$_2$)$_x$–]–wherein x is 0 or 1; or

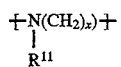

wherein x is 0 or 1 and $R^{11}$ is H or $C_1$–$C_5$ straight or branched alkyl;

m is an integer from 0 to 4; and $R^4$ is

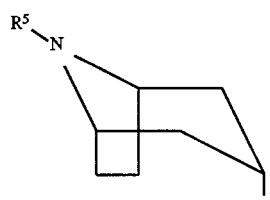

or

-continued

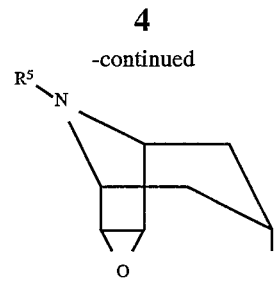

wherein $R^5$ is $C_1$–$C_5$ straight or branched alkyl; or $R^4$ is

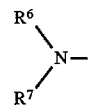

wherein each of $R^6$ and $R^7$, which may be the same or different, is selected from the group consisting of $C_1$–$C_5$ straight or branched alkyl, $C_6H_5$—$C_qH_{2q}$— wherein q is an integer from 1 to 4, phenyl optionally bearing 1 to 3 $C_1$–$C_4$ straight or branched alkyl substituents, and ($C_3$–$C_8$ cycloalkyl)-$C_pH_{2p}$— wherein p is an integer from 0 to 4 and wherein the 3- to 8-membered ring portion may optionally bear 1 to 4 $C_1$–$C_4$ straight or branched alkyl substituents, or wherein $R^6$ and $R^7$ are combined such that —$NR^6R^7$ represents the residue of a saturated monocyclic secondary amine; or $R^4$ is a radical of the formula

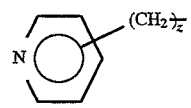

wherein z is an integer from 0 to 3; the acid additions salts of the compounds of formula (I) with acids of the formula HY wherein Y is a pharmaceutically acceptable anion; and the quaternary ammonium salts of the compounds of formula (I) with compounds of the formula $R^{12}Y$ wherein Y is defined as above and $R^{12}$ is $C_1$–$C_4$ straight or branched alkyl or benzyl.

The compounds of formula (I) and their salts are designed such that the ester group, —$COOR^1$, is metabolically hydrolyzable to the free alcohol ($R^1$—OH) and a non-toxic metabolite of an anticholinergic agent following administration to a human or non-human animal.

The invention further provides pharmaceutical compositions in unit dosage form comprising an anticholinergic or mydriasis-inducing effective amount of a compound of the above formula or an acid addition salt or quaternary ammonium salt thereof and a pharmaceutically acceptable carrier therefor; and antiperspirant compositions comprising an antiperspirant effective amount of said compound or salt and a non-toxic carrier therefor.

Finally, the invention also provides methods of treatment comprising administering to an animal or human in need thereof an anticholinergic or mydriasis-inducing or an antisecretory/antiperspirant effective amount of a compound of the above formula or salt thereof.

BRIEF DESCRIPTION OF THE DRAWING

FIG. 1 depicts the mydriatic activity of a representative compound of the invention (0.05% and 0.1%) in rabbits compared with tropicamide (0.1%).

DETAILED DESCRIPTION OF THE INVENTION

The invention is predicated on the discovery that certain esters of inactive polar acidic metabolites of atropine, scopolamine and other known anticholinergic compounds, as well as synthetic analogs thereof, are active anticholinergic compounds which are significantly less toxic than their parent free alcohols. Several have also been found to be active mydriatic agents which induce a much shorter duration of mydriasis than the parent free alcohols.

For example, the free acids having the structural formula:

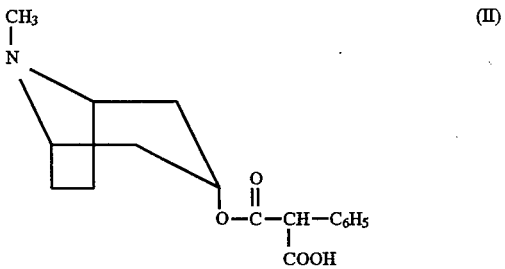

(II)

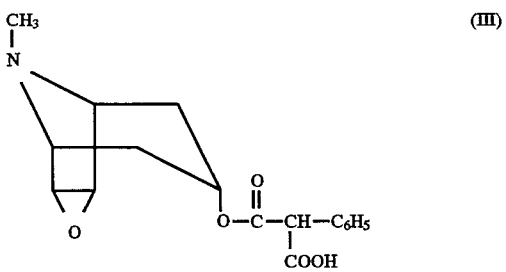

(III)

are anticholinergically inactive metabolites of atropine and scopolamine, respectively. Certain esters of these acids possess anticholinergic, mydriatic and antisecretory/antiperspirant properties equivalent to atropine and scopolamine but are far less toxic. The esters are metabolically hydrolyzed to the above inactive acidic metabolites (II) and (III) and non-toxic alcohols when administered to animals or humans.

The structural variables $R^2$, $R^3$, $R^4$ and m in formula (I) are selected such that those portions of the compound of formula (I) closely resemble the corresponding portions of a known anticholinergic agent. The $R^1$ substituent is selected such that it is metabolically hydrolyzable to the free alcohol and the inactive metabolite. All of the groups are selected such that they do not detrimentally affect the anticholinergic/mydriatic/antisecretory/antiperspirant properties of the compound or adversely affect the non-toxic nature of the compound. Preferably, when it is desired that the compound not enter the central nervous system, the compound of formula (I) is utilized in its quaternary salt form. The quaternary salts are also preferred in that they frequently possess higher anticholinergic/mydriatic/antisecretory/antiperspirant activity than the corresponding non-quaternized compounds.

With respect to the various groups encompassed by the generic terms used in this specification, the following definitions and explanations are applicable:

The alkyl groupings encompassed by the $R^1$, $R^2$, $R^3$, $R^5$, $R^6$, $R^7$, $R^8$, $R^9$, $R^{10}$, $R^{11}$ and $R^{12}$ structural variables in formula (I) include some or all of the following, depending on the specific carbon atom limitations expressed with formula (I) for the particular alkyl group involved: methyl, ethyl, propyl, butyl, pentyl, hexyl, heptyl and octyl, and their branched-chain isomers such as isopropyl, isobutyl and the like.

The alkenyl groupings encompassed by $R^1$ and $R^2$ in formula (I) can be exemplified by vinyl, propenyl and butenyl.

The optionally substituted $C_3$–$C_8$ cycloalkyl portion of the ($C_3$–$C_8$ cycloalkyl)-$C_pH_{2p}$— radicals encompassed by $R^1$, $R^2$, $R^3$, $R^6$ and $R^7$ in formula (I) can be exemplified by cyclopropyl, 2-methylcyclopropyl, 3-ethylcyclopropyl, 2-butylcyclopropyl, 3-pentylcyclopropyl, 2-hexylcyclopropyl, cyclobutyl, 2-methylcyclobutyl, 2,3-dimethylcyclobutyl, 3-butylcyclobutyl, 4-hexylcyclobutyl, 2,3,3-trimethylcyclobutyl, 3,3,4,4-tetramethylcyclobutyl, cyclopentyl, 2-methylcyclopentyl, 3-ethylcyclopentyl, 4-butylcyclopentyl, 5-methylcyclopentyl, 3-pentylcyclopentyl, 4-hexylcyclopentyl, 2,3-dimethylcyclopentyl, 2,2,5,5-tetramethylcyclopentyl, 2,3,4-trimethylcyclopentyl, 2,4-dimethyl-3-ethylcyclopentyl, 2,2,3,4,4-pentamethylcyclopentyl, 2,3-dimethyl-3-propylcyclopentyl, cyclohexyl, 4-methylcyclohexyl, 4-tert-butylcyclohexyl, 2,6-dimethylcyclohexyl, 3,5-dimethylcyclohexyl, 3,3,5,5-tetramethylcyclohexyl, 2-methylcyclohexyl, 2-ethylcyclohexyl, 4-propylcyclohexyl, 5-butylcyclohexyl, 2,3-dimethylcyclohexyl, 2,4-dimethylcyclohexyl, 2,5dimethylcyclohexyl, 2,3,4-trimethylcyclohexyl, 2,3-dimethyl-5-ethylcyclohexyl, 2,5-dimethyl-6-propylcyclohexyl, 2,4-dimethyl-3-butylcyclohexyl, 2,2,4,4-tetramethylcyclohexyl, 3,3,6,6-tetramethylcyclohexyl, 3,3,4,5,5-pentamethylcyclohexyl, 3,3,4,5,5,6-hexamethylcyclohexyl, 3,3,5-trimethyl-4-ethylcyclohexyl, 3,4,4-trimethyl-5-propylcyclohexyl, cycloheptyl, 3-methylcycloheptyl, 5-propylcycloheptyl, 6-butylcycloheptyl, 7-methylcycloheptyl, cyclooctyl, 2-methylcyclooctyl, 3-ethylcyclooctyl, 3,3,4-trimethylcyclooctyl, 3,3,5,5-tetramethylcyclooctyl and the like.

The optionally substituted $C_3$–$C_8$ cycloalkenyl portion of the ($C_3$–$C_8$ cycloalkenyl)-$C_pH_{2p}$— radicals encompassed by $R^1$ and $R^2$ in formula (I) can be exemplified by cyclopentenyl and cyclohexenyl and the like.

The ($C_6$–$C_{18}$ polycarbocyclic)-$C_pH_{2p}$— radicals encompassed by $R^1$ and $R^2$ in formula (I) have a total of 6 to 28 carbon atoms in the optionally substituted ($C_6$–$C_{18}$ polycarbocyclic) portion, i.e. 6 to 18 in the ring and 0 to 10 in the optional alkyl substituents. The ($C_6$–$C_{18}$ polycarbocyclic)-$C_pH_{2p}$— radicals can be exemplified by adamantyl (especially 1- or 2-adamantyl), adamantylmethyl (especially 1-adamantylmethyl), adamantylethyl (especially 1-adamantylethyl), bornyl [especially (1S)-endo-bornyl], norbonyl, (e.g. exo-norbornyl or endo-norbornyl), isopinocamphyl, norbornenyl (e.g. 5-norbornen-2-yl), norbornylmethyl (e.g. 2-norbornylmethyl) and norbornylethyl (e.g. 2-norbornylethyl), and by radicals of the type —$C_pH_{2p}$— (sterol residue)

wherein p is defined as above and the sterol residue is the portion of a steroidol alcohol which remains after removal of a hydrogen atom from a hydroxy group therein. The sterol residue may be that of a pharmacologically inactive steroid, e.g. cholesterol, a bile acid (cholic acid or related compound), 5α-androstan-3β-ol, epiandrosterone, androstenol, dehydroepiandrosterone, epicholestanol or the like.

When $R^6$ and $R^7$ in formula (I) are combined such that —$NR^6R^7$ represents the residue of a saturated monocyclic secondary amine, such monocycles preferably have 5 to 7 ring atoms optionally containing another hereto atom (—O—, —S— or —N—) in addition to the indicated nitrogen atom, and optionally bear one or more, preferably 1 or 2, substituents such as phenyl, benzyl and methyl. Illustrative of residues of saturated monocyclic secondary amines which are encompassed by the —NR$^6$R$^7$ term are morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino and 4-phenyl-1-piperazinyl.

The pharmaceutically acceptable acids HY with which the compounds of formula (I) can form pharmaceutically acceptable acid addition salts can be illustrated by inorganic acids such as hydrochloric acid, sulfuric acid, hydrobromic acid and the like; and by organic acids such as acetic acid, oxalic acid, succinic acid, maleic acid, fumaric acid, malic acid, tartaric acid, citric acid, malonic acid, methanesulfonic acid, benzoic acid and the like.

The compounds of the formula R$^{12}$Y with which the compounds of formula (I) can form pharmaceutically acceptable quaternary ammonium salts can be illustrated by alkyl and benzyl halides (iodides, chlorides and bromides, especially CH$_3$Br, CH$_3$I and CH$_3$Cl) and the corresponding dialkylsulfates, e.g. dimethylsulfate. However, Y can be any pharmaceutically acceptable anion, e.g. halogen, sulfate, alkylsulfate or alkylsulfonate, as in the case of the acid addition salts.

Preferred compounds of formula (I) include those in which the structural variables are as follows:

R$^1$ is alkyl (especially methyl, ethyl, isopropyl, n-propyl, isobutyl, n-butyl, n-pentyl, n-hexyl, n-heptyl or n-octyl), cycloalkyl-C$_p$H$_{2p}$— (especially cyclohexyl, cyclopentyl, cyclopropylmethyl, 2-methylcyclohexyl, 4-methylcyclohexyl, 4-tert-butylcyclohexyl, 3,5-dimethylcyclohexyl, 2,6-dimethylcyclohexyl, cyclohexylmethyl or cyclohexylethyl) or polycarbocyclic-C$_p$H$_{2p}$— [especially adamantylmethyl, adamantylethyl, norbornylmethyl, norbornylethyl, isopinocamphyl, endo-norbornyl, exo-norbornyl or (1S)-endo-bornyl];

R$^2$ is phenyl, cyclopentyl or cyclohexyl;

R$^3$ is H, phenyl, cyclopentyl or cyclohexyl;

n is 0 or 1;

X is

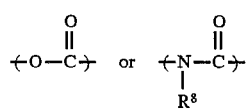

where R$^8$ is H, CH$_3$ or C$_2$H$_5$, or X is —CH$_2$—;

m is 0, 1 or 2; and

R$^4$ is

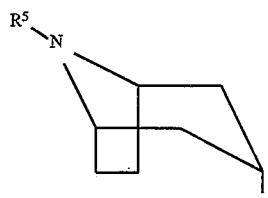

or

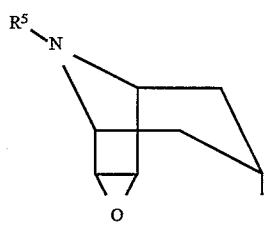

wherein R$^5$ is

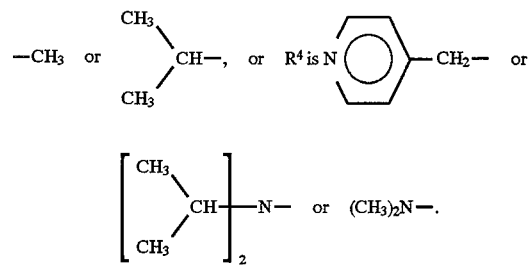

The quaternary ammonium salts of these compounds are particularly preferred.

The compounds of the present invention can be referred to as "soft drug" analogs or derivatives of the corresponding active alcohols.

Soft drug mydriatic/antiperspirant agents according to the present invention are illustrated in the following Table A which exemplifies several drugs based upon the above structural formula I.

TABLE A

1. Tropicamide Soft Drug

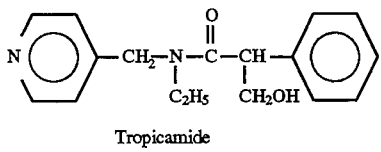

Tropicamide

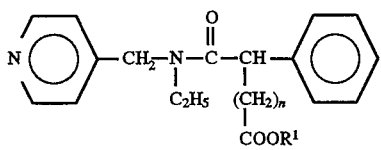

Soft Drug

$R^1$ = lower alkyl (1 to 8 carbon atoms)
n = 0 to 4
$R^2$ = Phenyl or other aryl or cycloalkyl
$R^3$ = H $X = -\underset{R_8}{N}-\overset{O}{\underset{\|}{C}}$-(amide)   $R^8 = -C_2H_5$ m = 0

$R^4 = $ pyridyl-CH$_2$—   z = 1

2. Isopropamide Soft Drug

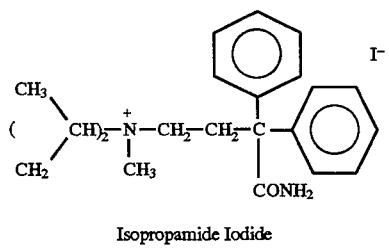

Isopropamide Iodide

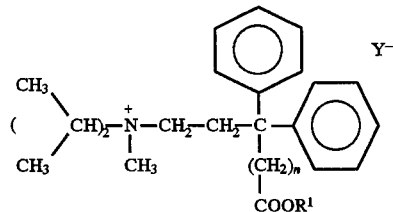

Soft Drug $R^1$ = lower alkyl (1 to 8 carbon atoms)
$R^2$, $R^3$ = Phenyl or other aryl or cycloalkyl
n = 0 to 4
X = —CH$_2$-(carbon atoms)
m = 1

$R^4 = \underset{R^7\ R^{12}}{\overset{R^6}{\diagdown}} N^+ —$   $R^6, R^7 = (CH_3)_2CH—$
$R^{12} = —CH_3$ $Y^-$ = anion, preferably halogen, alkyl sulfate, sulfate or alkylsulfonate

TABLE A-continued

3. Ipratropium Soft Drug

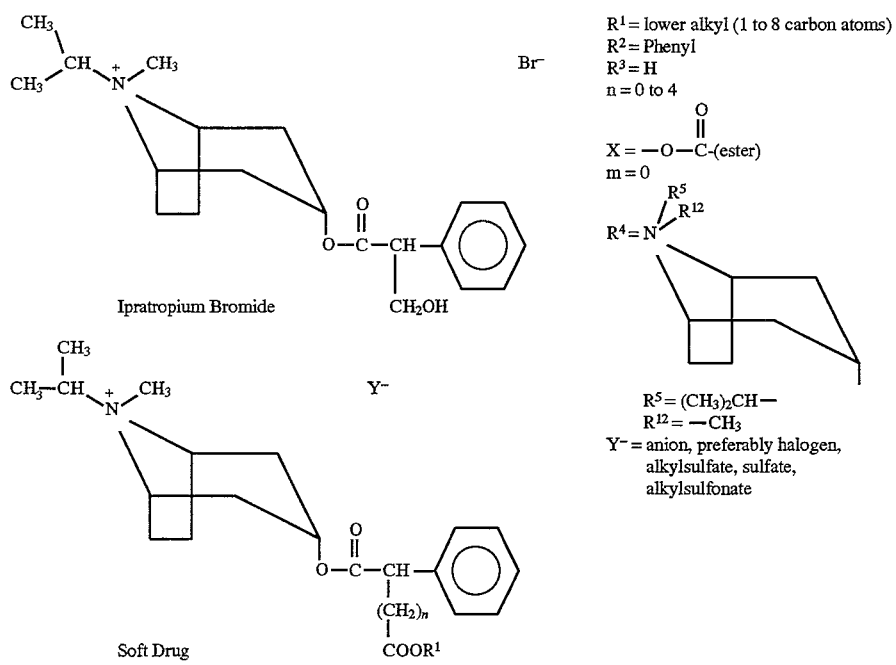

4. Cyclopentolate Soft Drug

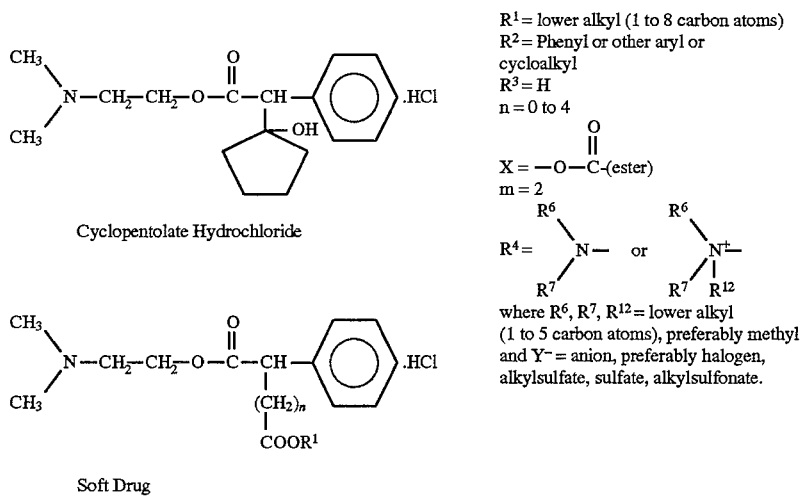

The compounds of the present invention can be synthesized in a variety of ways, the method of choice depending upon the particular compound involved, particularly on the identity of the X and n groupings. Typical synthetic routes are illustrated below for each of the categories of X values encompassed by formula (I). In the reaction schemes which follow, structural variables are as defined with formula (I) except as otherwise specified.

SCHEME I

PREPARATION OF ESTERS AND AMIDES, i.e. COMPOUNDS OF FORMULA (I) WHEREIN X IS $-(O-\overset{O}{\underset{\|}{C}})-$ OR $-(N-\overset{O}{\underset{\|}{C}})-$:
$\phantom{XXXXXXXXXXXXXXXXXXXXXXXXXXXXXXXXXXX}\underset{R_8}{|}$ PART A - when n = 0:

-continued
SCHEME I

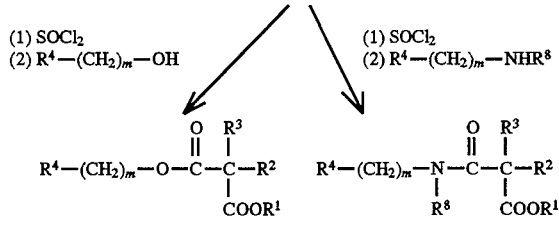

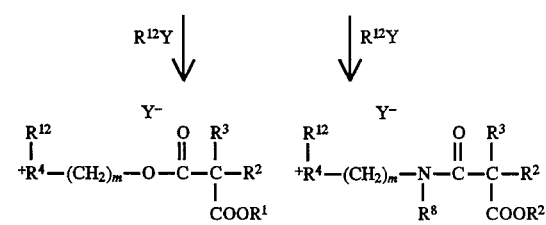

The esters and amides are thus prepared in two stages to the tertiary compounds and in three stages to the quaternary compounds from the starting diacid. When $R^2$ is phenyl and $R^3$ is hydrogen, the starting acid is phenylmalonic acid. A typical reaction is depicted below:

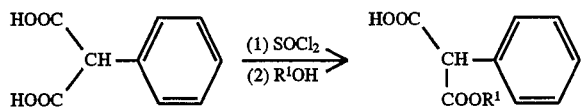
phenylmalonic acid

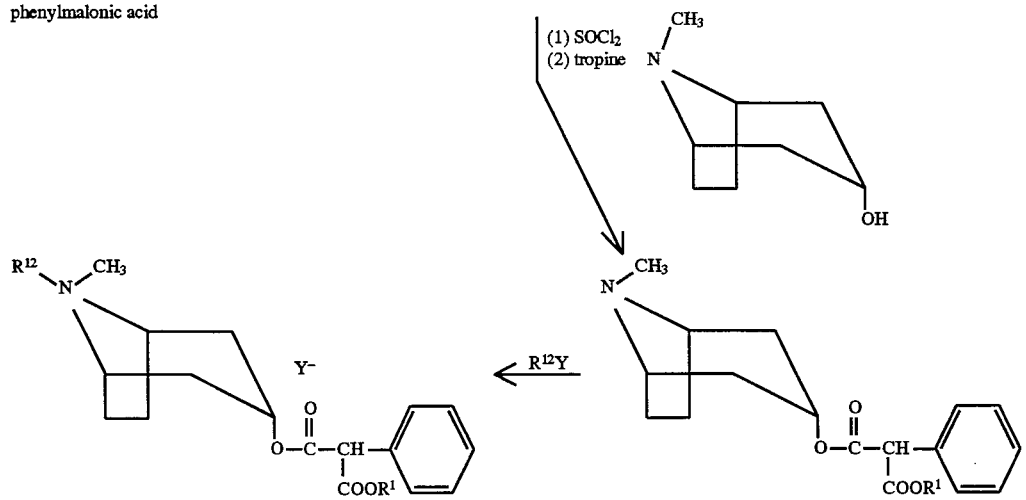

Thus, use of tropine as the alcohol reactant in the second esterification generates an atropine soft drug. Selection of other alcohol or amine reactants in the second esterification/amidation affords soft drugs corresponding to other anticholinergic agents, e.g. use of the alcohol $(CH_3)_2NCH_2CH_2OH$ generates a cyclopentolate soft drug, use of the amine

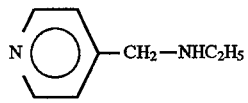

generates a tropicamide soft drug, use of the alcohol

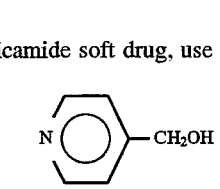

generates a tropicamide ester analog soft drug and so forth.

PART B - when n = 0, 1, 2, 3 or 4:

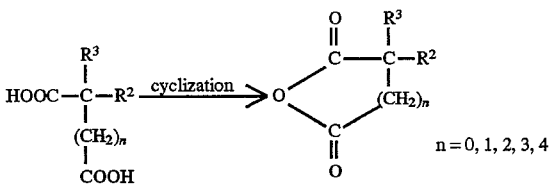

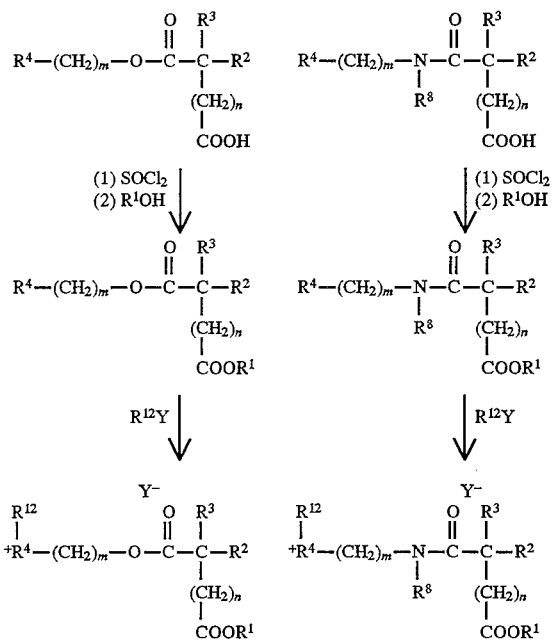

In this sequence, the anticholinergic ester or amide grouping is added prior to the $R^1OH$ reactant, which completes the soft portion of the molecule. In the first esterification/amidation, use of tropine ultimately affords an atropine soft drug, use of $(CH_3)_2NCH_2CH_2OH$ generates a cyclopentolate soft drug, use of

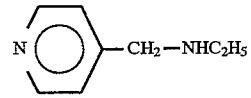

gives a tropicamide soft drug and so forth. Typical starting acids include phenylsuccinic acid (n=1) and phenyladipic acid (n=2).

SCHEME II

PREPARATION OF ETHERS, AMINES and THIOETHERS, X BEING $-O(CH_2)_x-$, $-N(CH_2)_x-$ or $-S(CH_2)_x-$:
$\qquad\qquad\qquad\quad\;\; |$
$\qquad\qquad\qquad\;\;\;R^{11}$

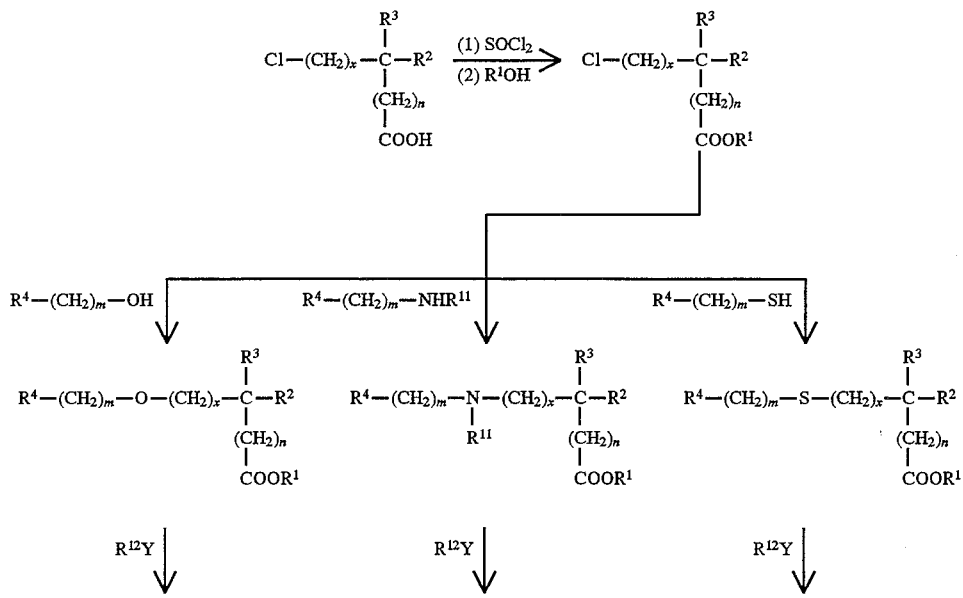

SCHEME II -continued

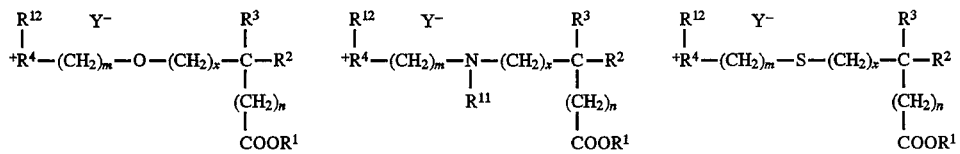

In a specific embodiment, the starting acid can have the formula

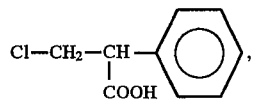

the alcohol reactant in the second esterification can be tropine, the amine reactant can be

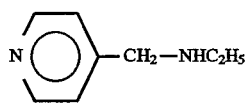

and the thiol reactant can be

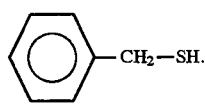

SCHEME III

PREPARATION OF COMPOUNDS IN WHICH X IS $-\overset{R^9}{\underset{R^{10}}{C}}-$:

METHOD A:

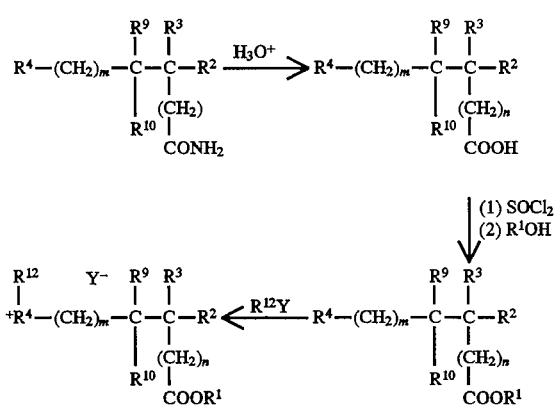

In one embodiment of this method, the starting amide is isopropamide iodide, which has the structure

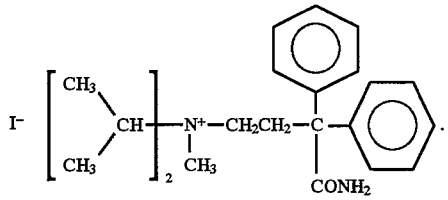

METHOD B:

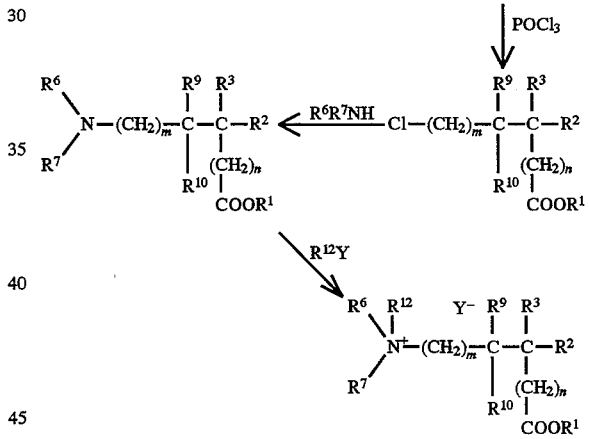

In a specific embodiment of Method B, the starting acid has the structure

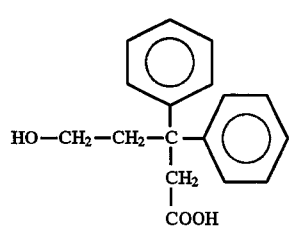

and the amine reactant $R^6R^7NH$ is diisopropylamine.

METHOD C:
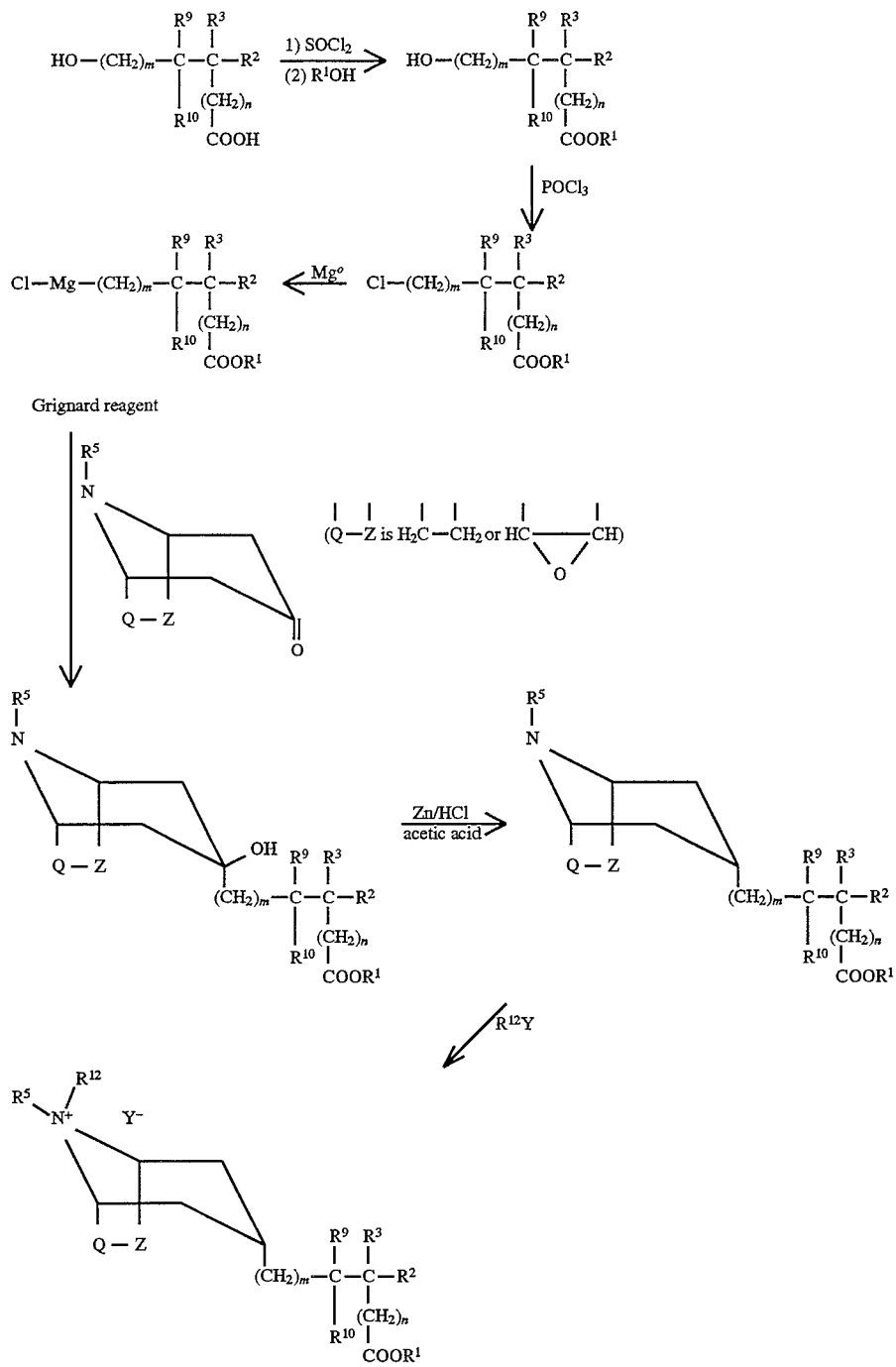
In a specific embodiment of Method C, the starting acid has the same structure as in the preceding Method B and the ketone reactant in the fourth step is tropinone, which has the structure

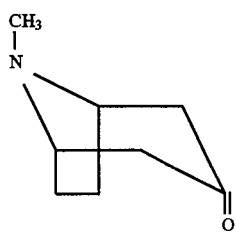

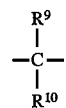

in the acid starting material as well as by selection of the ketone reactant. When X in formula (I) is

METHOD D:

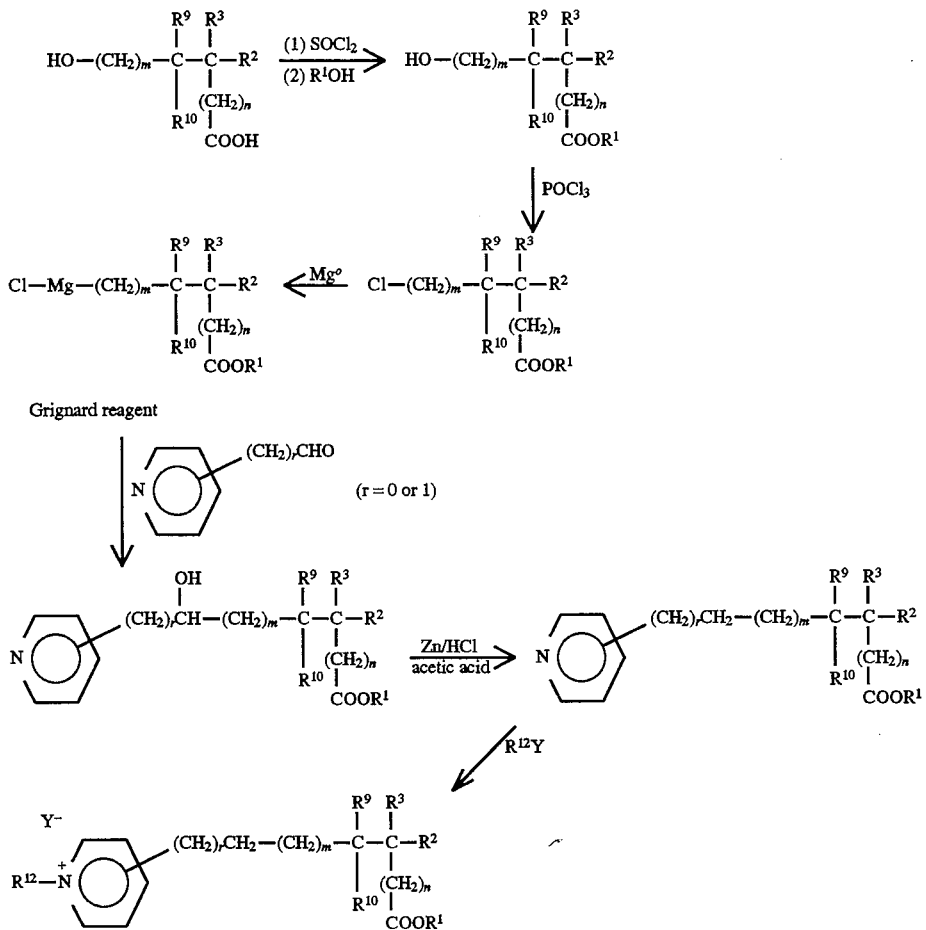

Again, in a specific illustration of the method, the same starting acid as employed in Methods B and C can be used. To obtain a soft drug isosteric with tropicamide, the ketone reactant in the fourth step can be

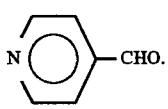

The length of the alkylene chain —$(CH_2)_rCH_2$—$(CH_2)_m$— in the final product can be adjusted by selection of $(CH_2)_m$ and $R^4$ is

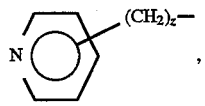

then m and z are not simultaneously zero.

SCHEME IV

PREPARATION OF KETONES (X = —C(=O)—):

METHOD A:

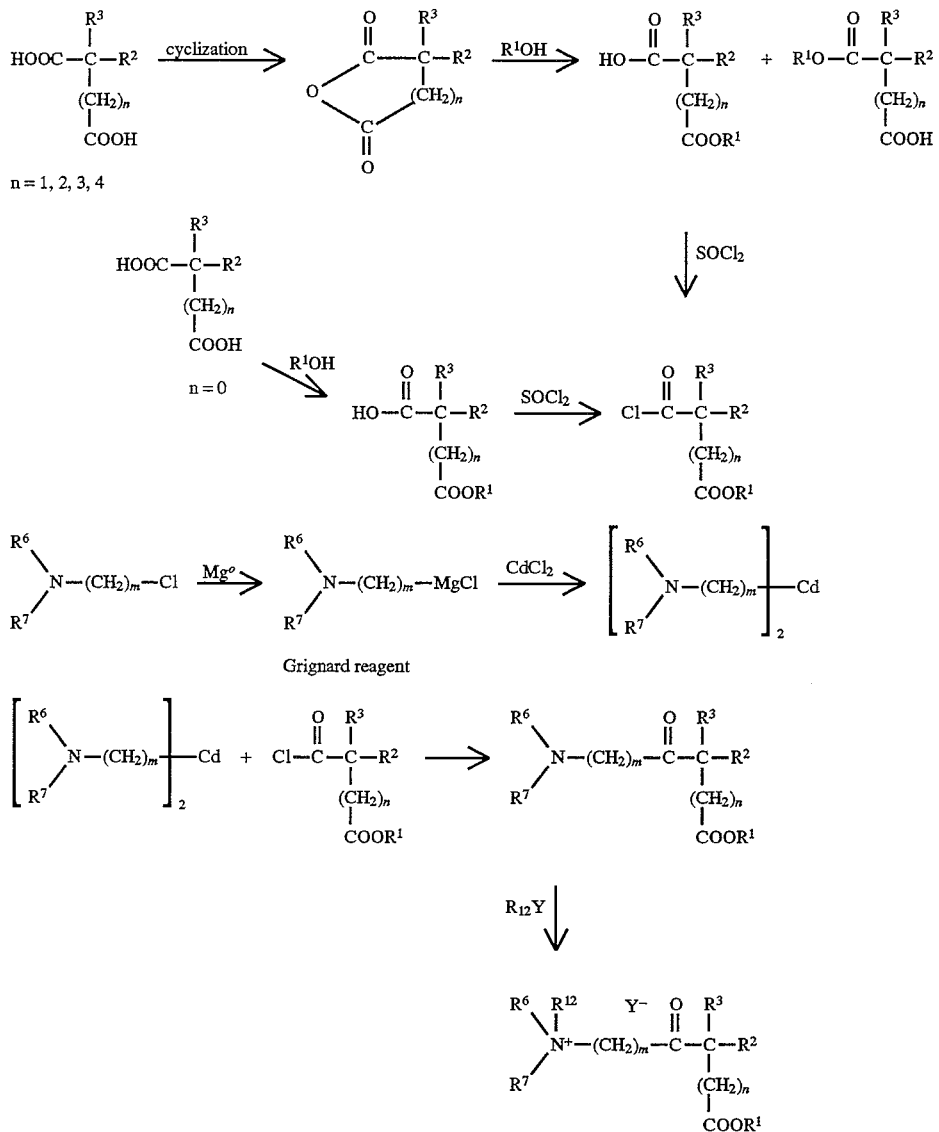

Preferred starting acids are those in which n=0 or 1, especially phenylmalonic acid and phenylsuccinic acid. In the case of phenylsuccinic acid, the product of the cyclization step, phenylsuccinic anhydride, is commercially available and can be employed in the racemic form or as a pure isomer (preferably the d, l or 1 form). When X in formula (I) is

and $R^4$ is

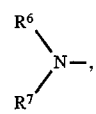

then m is greater than or equal to 1, i.e. m=1 to 4.

METHOD B:
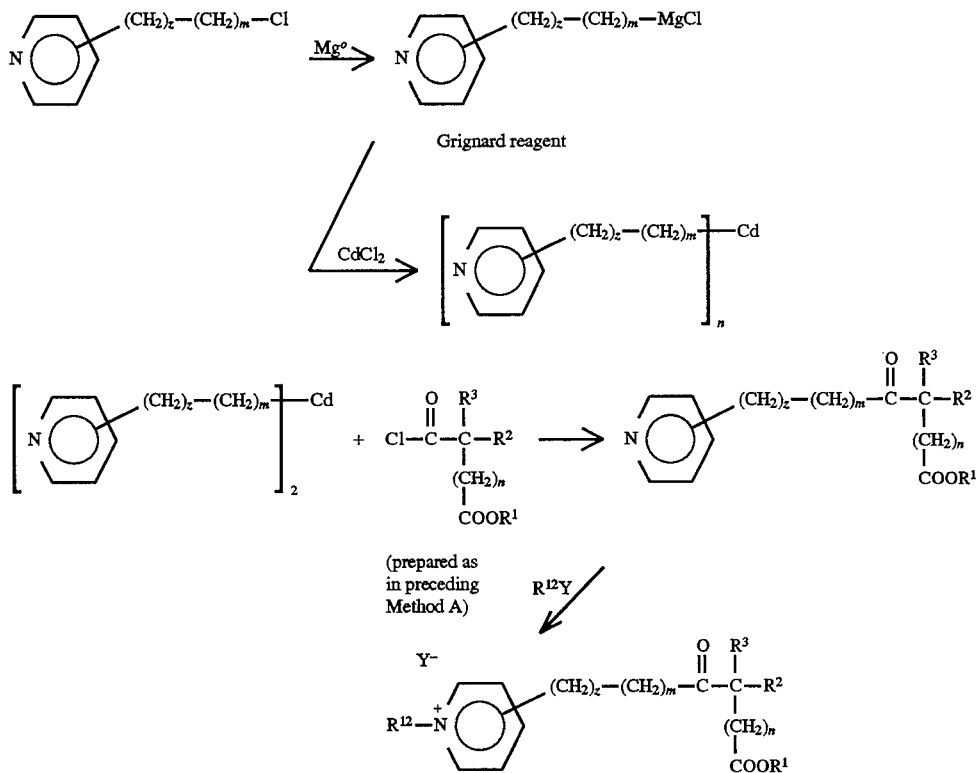
Preferred embodiments are derived from phenylmalonic acid and phenylsuccinic acid/phenylsuccinic anhydride, as described in the preceding Method A. When X in formula (I) is
and $R^4$ is
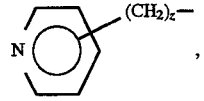
then m and z are not simultaneously zero.

METHOD C:

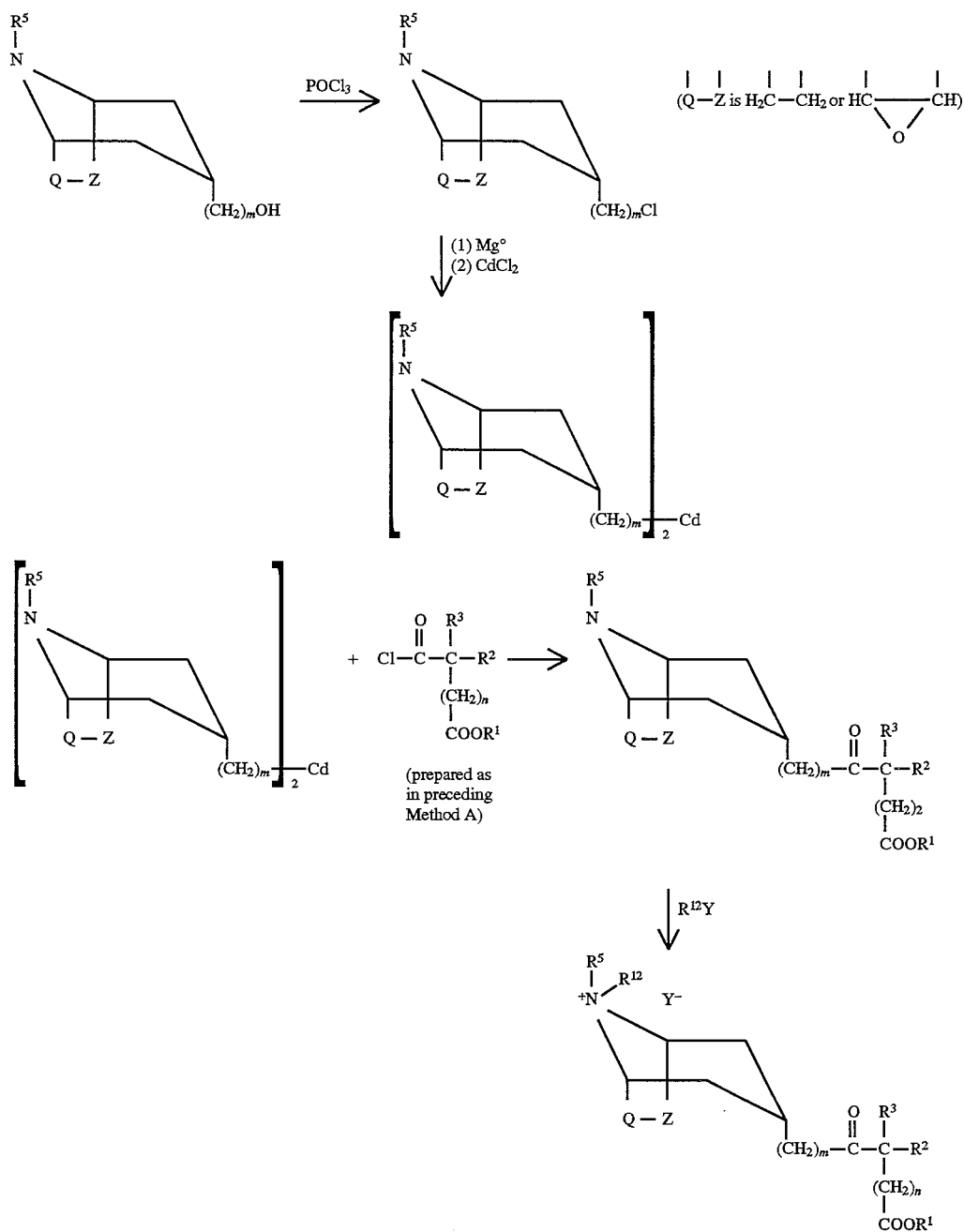

In preferred embodiments of Method C, n=0 or 1, i.e. the compounds are derived from phenylmalonic acid and phenylsuccinic acid/phenylsuccinic anhydride, as described in the preceding Method A. The preferred alcohol reactant in the first step is tropine $$\begin{array}{c} | \quad | \\ (Q-Z \end{array}$$

is $$\begin{array}{c} | \quad | \\ CH_2-CH_2, \end{array}$$

$R^5$ is $CH_3$ and m is zero) or scopine $$\begin{array}{c} | \quad | \\ (Q-Z \end{array}$$

is

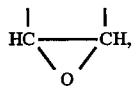

$R^5$ is $CH_3$ and m is zero.

Soft drug anticholinergic, mydriatic and antisecretory agents according to the present invention are illustrated in the following Table B which shows several drugs based upon above structural formula I. These derivatives can be prepared according to the one or more of the reaction schemes depicted above, utilizing the appropriate reactants:

TABLE B

| R¹ | R² | R³ | R⁴ or R⁴/R¹² | m (0 to 4) | n (0 to 4) | X | Y⁻ |
|---|---|---|---|---|---|---|---|
| Lower alkyl, cyclic, straight or branched chain alcohols (1 to 8 carbon atoms) | phenyl | H | 3-pyridyl-CH₂– | 0 | 0 | –N(C₂H₅)–C(=O)– | Any pharmaceutically acceptable anion, halogen, sulfate, alkylsulfate or alkylsulfonate |
| CH₃– | phenyl | phenyl | [(CH₃)₂CH–N⁺(CH₃)–]₂ | 1 | 0 | –CH₂– | Br⁻ |
| CH₃CH₂– | phenyl | H | quinuclidinium (CH₃–N⁺, CH₃) | 0 | 0 | –O–C(=O)– | I⁻ |
| CH₃CH₂CH₂– | phenyl | H | CH₃–N(CH₃)– | 2 | 0 | –O–C(=O)– | I⁻ |
| CH₃–CH(CH₃)– | phenyl | phenyl | quinuclidinium epoxide (CH₃–N⁺, CH₃, O) | 0 | 0 | –O–C(=O)– | CH₃SO₄⁻ |
| CH₃(CH₂)₂CH₂– | cyclohexyl | cyclohexyl | quinuclidinium (CH₃–N⁺, CH₃) | 0 | 0 | –O–C(=O)– | CH₃SO₃⁻ |

TABLE B-continued

| R¹ | R² | R³ | R⁴ or R⁴/R¹² | m (0 to 4) | n (0 to 4) | X | Y⁻ |
|---|---|---|---|---|---|---|---|
| CH₃(CH₂)₃—CH₂— | phenyl | H | N⁺(CH₃)₂-bicyclic | 0 | 1 | —O—C(=O)— | 4-Br-C₆H₄-SO₃⁻ |
| CH₃(CH₂)₄CH₂— | phenyl | H | N⁺(CH₃)₂-bicyclic | 0 | 2 | —O—C(=O)— | Cl⁻ |
| CH₃(CH₂)₅CH₂— | —CH₂-phenyl | H | N⁺(CH₃)₂-bicyclic | 0 | 3 | —O—C(=O)— | 4-CH₃-C₆H₄-SO₃⁻ |
| CH₃(CH₂)₆CH₂— | cyclopentyl | cyclopentyl | N-piperidinyl | 1 | 4 | —O— | I⁻ |
| CH₃CH₂—CH(CH₃)— | CH₂CH₂CH₃ | H | N⁺(CH₃)₂-bicyclic | 0 | 2 | —O—C(=O)— | I⁻ |

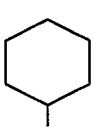

TABLE B-continued

| $R^1$ | $R^2$ | $R^3$ | $R^4$ or $R^4/R^{12}$ | m (0 to 4) | n (0 to 4) | X | Y⁻ |
|---|---|---|---|---|---|---|---|
| $CH_3-CH-CH_2-CH_2-$<br>　　$\|$<br>　　$CH_3$ | 3,5-dimethylcyclohexyl | cyclohexyl | $CH_3-N\underset{\phantom{x}}{\overset{\phantom{x}}{\bigcirc}}N-$ (piperazinyl) | 1 | 0 | $-NH-\overset{O}{\underset{\|}{C}}-$ | — |
| cyclopropyl-$CH_2-$ | phenyl | $-CH_2-$phenyl | $CH_3-\underset{\underset{CH_3}{\|}}{\overset{\overset{CH_3}{\|}}{N^+}}-$ | 2 | 0 | $-O-$ | Cl⁻ |

The rates of metabolic hydrolysis of the active esters may be controlled by selection of the esterifying alcohol.

The invention is illustrated by the following non-limiting examples.

EXAMPLE 1

Methyl Hydrogen Phenylmalonate

A mixture of phenylmalonic acid (3.6 g, 0.02 mol), boron trifluoride etherate (2.4 mL, 0.02 mol) and 0.8 mL of anhydrous methanol (0.02 mol) was refluxed and stirred for 24 hours. After cooling to room temperature, the reaction mixture was filtered and 20 mL of water was added.

The precipitated oil was extracted with $CHCl_3$ (30 mL×3). The combined extracts were washed with water and dried over anhydrous $MgSO_4$ and evaporated under reduced pressure. The oily liquid obtained showed NMR spectra consistent with its structure.

$R_f$ of the acid: 0.52 yield: 57% $R_f$ of the ester: 0.72.

Preparation of Methyl Phenylmalonyl Chloride

To the oily liquid obtained above was added 5 mL of thionyl chloride. The reaction mixture was heated on an oil bath for one hour under anhydrous conditions. The excess thionyl chloride was removed by the addition and the in vacuo distillation of 10 mL of anhydrous benzene. The product was oily and was reacted immediately with tropine base.

Esterification of Methyl Phenylmalonyl Chloride and Tropine

Thoroughly dried tropine (1.4 g, 0.01 mol) was added to the freshly prepared methyl hydrogen phenylmalonyl chloride. The mixture was heated for 5 hrs at 100° C., with stirring, under anhydrous conditions. The mixture turned brown and gas evolved. After cooling to room temperature and filtration, the mixture was treated with 10 mL of water. The clear solution was adjusted to pH 9 with saturated $Na_2CO_3$ solution, extracted with ethyl ether and dried over anhydrous $MgSO_4$. The ethereal solution was filtered and distilled under reduced pressure to produce an oily product.

EXAMPLE 2

Preparation of (±)-8-Methyl-8-azabicyclo[3.2.1]oct-3-yl (α-Ethoxycarbonyl-α-phenyl)acetate a) Preparation of ethyl hydrogen phenylmalonate Phenylmalonic acid (13.5 g, 0.07 mol) in dry ether (40 mL) was treated with thionyl chloride (8.92 g, 5.4 mL, 0.07 mol) and one drop of N,N-dimethylformamide. The mixture was heated at 40°–50° C. for 3 hours. The clear solution was evaporated under reduced pressure to remove any residual thionyl chloride. The oily residue was redissolved in dry ether (40 mL), the solution was treated with ethanol (0.075 mol, 4.1 mL) and refluxed for 2 hours. The reaction mixture was cooled to room temperature and washed with water. The organic layer was extracted with saturated solution of sodium bicarbonate until alkaline. The combined extracts were washed with ether and the aqueous layer was acidified with 5N HCl to pH 1. The precipitated oil was extracted with $CH_2Cl_2$ (50 mL×3). The combined extracts were washed with water (50 mL×4) and dried over anhydrous $MgSO_4$. The oily product crystallized on standing.

Yield: 7.2 g (49.4%) M.p.: 78°–9° C. (as reported).

b) Preparation of ethyl phenylmalonyl chloride

Ethyl hydrogen phenylmalonate (2.08 g, 0.01 mol) was mixed with thionyl chloride (5 mL) and heated at 70° C. for one hour under anhydrous conditions. The liquid thus obtained was evaporated under reduced pressure. Anhydrous benzene (10 mL) was added to the residue and redistilled to remove any residual thionyl chloride.

c) Esterification of ethyl phenylmalonyl chloride and tropine

The previously obtained acid chloride (0.01 mol) dissolved in 10 mL of dry benzene was added dropwise with stirring for half an hour to a solution of dry tropine (2.8 g, 0.02 mol) in dry benzene. The mixture was stirred at room temperature for 24 hours and filtered. The filtrate was washed with water until neutral. The organic layer was dried over anhydrous $MgSO_4$ and the solvent was evaporated. The obtained oily base was converted into the oxalate salt by adding an ether solution of oxalic acid to a solution of the base in ether. By scratching the mixture, a white solid product was obtained. When cooled in a deep freezer, then washed with cold ether and dried for 24 hours in a desiccator over $CaCl_2$, the crystalline product represented 78% conversion to oxalate.

Recrystallization was carried out from a methanol-ether mixture.

$R_f$ of the free base: 0.4 Yield of the free base: 75% Yield of the oxalate: 78% M.p. 135°–7° C.

| Anal for $C_{19}H_{25}O_4N.(COOH)_2$ | | | |
|---|---|---|---|
| | C % | H % | N % |
| Theoretical | 59.85 | 6.45 | 3.32 |
| Found | 59.88 | 6.52 | 3.30 |

According to the microanalytical data and NMR spectra, the compound obtained has the following structure:

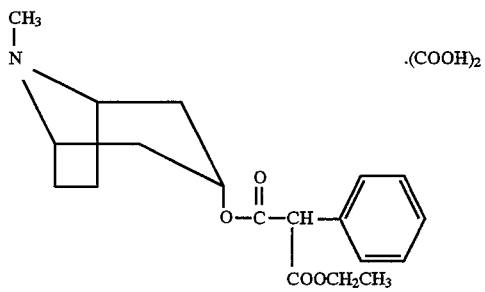

EXAMPLE 3

Preparation of (±)-8-Methyl-8-azabicyclo[3.2.1]oct-3-yl (α-Methoxycarbonyl-α-phenyl)acetate a) Synthesis of methyl hydrogen phenylmalonate (new method)

Phenylmalonic acid (13.5 g, 0.07 mol) in dry ether (40 mL) was treated with thionyl chloride (8.92 g, 5.4 mL, 0.07 mol) and one drop of N,N-dimethylformamide. The mixture was heated at 40°–50° C. for 3 hours. The clear solution was evaporated under reduced pressure to remove any residual thionyl chloride. The oily residue was redissolved in dry ether (40 mL) and the solution was treated with methyl alcohol (0.075 mol, 3 mL) and refluxed for 2 hours. The reaction mixture was cooled to room temperature and washed with water. The organic layer was extracted with saturated solution of sodium bicarbonate until alkaline. The combined extracts were washed with ether and the aqueous layer acidified with 5N HCl to pH 1. The precipitated oil was extracted with $CH_2Cl_2$ (50 mL×3). The combined extracts were washed with water (50 mL×4) and dried over anhydrous $MgSO_4$. The oily product crystallized on standing.

Yield: 6 g (41.2%) M.p.: 86°–88° C. as reported.

b) Synthesis of methyl phenylmalonyl chloride

The previously prepared ester (2.94 g, 0.01 mol) was mixed with thionyl chloride (5 mL) and heated at 70° C. for one hour under anhydrous conditions. The liquid obtained was evaporated under reduced pressure. Anhydrous benzene (10 mL) was added to the residue and redistilled to remove any residual thionyl chloride.

c) Esterification of methyl phenylmalonyl chloride and tropine

The previously prepared acid chloride was dissolved in 10 mL of dry benzene and was added dropwise with stirring for half an hour to a solution of dry tropine (2.8 g, 0.02 mol) in dry benzene. The mixture was stirred at room temperature for 24 hours and filtered. The filtrate was washed with water until neutral. The organic layer was dried over anhydrous $MgSO_4$ and the solvent was evaporated. The oily base thus obtained was purified by conversion into the oxalate salt by adding an ether solution of oxalic acid to a solution of the base in ether. By scratching the mixture and keeping in a refrigerator overnight, a white solid product was separated. Rapid filtration and drying in a vacuum desiccator over anhydrous $CaCl_2$ were carried out.

Recrystallization from methanol-ether mixture gave white crystalline product.

$R_f$ of the free base: 0.41 Yield of the free base: 1 g (64.5%) Yield of the oxalate: 1.5 g (35.7%) M.p.: 89°–91° C.

| Anal. for $C_{18}H_{23}O_4N.(COOH)_2.H_2O$: | | | |
|---|---|---|---|
| | C % | H % | N % |
| Theoretical | 56.47 | 6.39 | 3.29 |
| Found | 56.48 | 6.2 | 2.94 |

According to the microanalytical data and NMR spectra, the compound has the following structure:

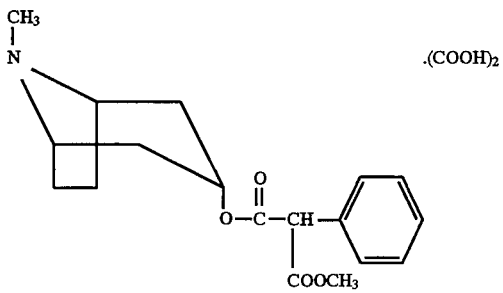

EXAMPLE 4

Preparation of (±)-8-Methyl-8-azabicyclo[3.2.1]oct-3-yl (α-Isopropoxycarbonyl-α-phenyl)acetate a) Synthesis of isopropyl hydrogen phenylmalonate Phenylmalonic acid (13.5 g, 0.07 mol) in dry ether (40 mL) was treated with thionyl chloride (8.92 g, 5.4 mL, 0.07 mol) and one drop of N,N-dimethylformamide. The mixture was heated at 40°–50° C. for 3 hours. The clear solution was evaporated under reduced pressure to remove any residual thionyl chloride. The oily residue was redissolved in dry ether (40 mL), and the solution was treated with isopropyl alcohol (0.075 mol, 5.76 mL), refluxed for 2 hours and worked up as before to give the titled compound.

Yield=60% (as reported) M.p.: 64°–66° C. (as reported).

b) Synthesis of isopropyl phenylmalonyl chloride

The previously prepared monoester (2.22 g, 0.01 mol) was mixed with thionyl chloride (5 mL) and heated at 70° C. for one hour under anhydrous conditions. The liquid thus obtained was evaporated under reduced pressure. Anhydrous benzene (10 mL) was added and the mixture was redistilled.

c) Esterification of isopropyl phenylmalonyl chloride and tropine

The previously prepared acid chloride was dissolved in 10 mL of dry benzene and added dropwise with stirring for half an hour to a solution of dry tropine (2.8 g, 0.02 mol) in dry benzene. The mixture was stirred at room temperature for 24 hours and filtered. The filtrate was washed with water until neutral. The organic layer was dried over anhydrous $MgSO_4$ and the solvent was evaporated. The oily base thus obtained was purified by formation of the oxalate salt. An ether solution of oxalic acid was added to an ether solution of the base. By scratching the mixture and keeping in a deep freezer for 24 hours, a white solid product was obtained. Filtration followed by drying in a vacuum desiccator over $CaCl_2$ was carried out.

Recrystallization from methanol-ether mixture gave a white crystalline product.

$R_f$ of the base: 0.3 Yield of the base: 2.5 g (72.4%) Yield of the oxalate: 3 g (68.9%) M.p.: 78°–80° C.

| Anal. for $C_{20}H_{27}O_4N.(COOH)_2$. | | | |
|---|---|---|---|
| | C % | H % | N % |
| Theoretical | 60.68 | 6.71 | 3.21 |
| Found | 60.41 | 6.77 | 3.13 |

According to both microanalytical data and NMR spectra, the compound obtained has the following structure:

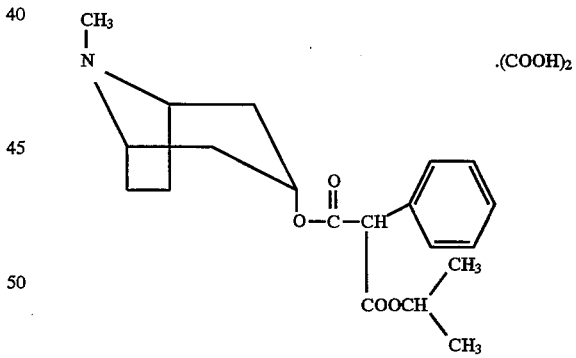

EXAMPLE 5

Preparation of (±)-8-Methyl-8-azabicyclo[3.2.1]oct-3-yl (α-Cyclohexyloxycarbonyl-α-phenyl)acetate a) Preparation of cyclohexyl hydrogen phenylmalonate Phenylmalonic acid (13.5 g, 0.07 mol) in dry ether (40 mL) was treated with thionyl chloride (8.92 g, 5.4 mL, 0.07 mol) and one drop of N,N-dimethylformamide. The mixture was heated at 40°–50° C. for 3 hours. The clear solution was distilled under vacuum. The oily residue was redissolved in dry ether (40 mL), the solution was treated with cyclohexyl alcohol (0.075 mol, 7.9 mL) and refluxed for 2 hours. The mixture was worked up as before to give an oily product which crystallized on standing. Recrystallization was carried out from a benzene-petroleum ether (40°–60°) mixture to give a white crystalline product.

$R_f$: 0.76 M.p.: 80°–2° C. Yield: 12.5 g (64.14%).

| Anal. for $C_{15}H_{18}O_4$ | | |
|---|---|---|
| | C % | H % |
| Theoretical | 68.69 | 6.9 |
| Found | 68.79 | 6.92 |

According to microanalytical and NMR data, the synthesized compound has the following structure:

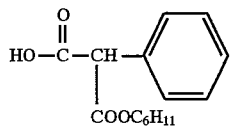

b) Synthesis of cyclohexyl phenylmalonyl chloride

The cyclohexyl ester prepared above (2.6 g, 0.01 mol) was mixed with thionyl chloride (5 mL) and heated at 70° C. for one hour under anhydrous conditions. The liquid obtained was evaporated under reduced pressure. Anhydrous benzene (10 mL) was added to the residue and redistilled again to remove any residual thionyl chloride. The oily product was solidified on standing and was used for the next step without further purification.

c) Esterification of cyclohexyl phenylmalonyl chloride and tropine

The acid chloride was dissolved in 10 mL of dry benzene and added dropwise with stirring for half an hour to a solution of dry tropine (2.8 g, 0.02 mol) in dry benzene. The mixture was stirred at room temperature for 24 hours and filtered. The filtrate was washed with water until neutral. The organic layer was dried over anhydrous $MgSO_4$ and the solvent was evaporated. The obtained oily base was converted into its oxalate salt by adding an ether solution of oxalic acid to a solution of the base in ether. By scratching the mixture and cooling in a refrigerator, a white solid product was separated. Filtration and drying over $CaCl_2$ in a vacuum desiccator was carried out. On recrystallization from a methanol-ether mixture, a white crystalline product was obtained.

$R_f$: 0.22 Yield of the base: 3 g, 77% Yield of the oxalate: 3.1 g, 63% M.p.: 160°–2° C.

| Anal. for $C_{23}H_{31}NO_4.(COOH)_2$ | | | |
|---|---|---|---|
| | C % | H % | N % |
| Theoretical | 63.15 | 6.99 | 2.94 |
| Found | 63.05 | 7.26 | 2.78 |

Based on the microanalytical data and NMR spectra, the compound obtained has the following structure:

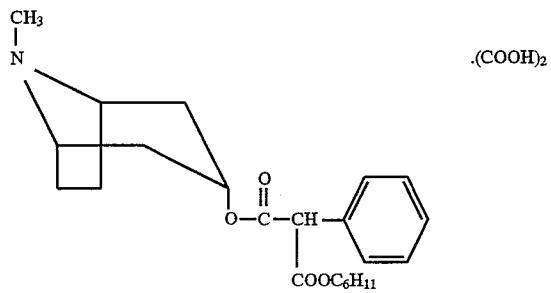

EXAMPLE 6

Preparation of Tropanyl Hydrogen Phenylmalonate or (±)-8-Methyl-8-azabicyclo[3.2.1]oct-3-yl (α-Carboxy-α-phenyl)acetate Phenylmalonic acid (2.5 g, 0.014 mol) in dry ether (10 mL) was treated with thionyl chloride (1.78 g, 1.09 mL, 0.01 mol), and N,N-dimethylformamide (two drops). The mixture was heated at 50°–60° C. for 2 hr. Ether and excess thionyl chloride were removed and three separate portions of dry benzene were added and removed the same way. The residue (1.9 gm, 0.01 mol) was dissolved in 20 mL dry benzene and added dropwise over a period of 0.5 hr to a stirred solution of dry tropine (2.82 g, 0.02 mol) in 10 mL dry benzene. The mixture was stirred at ambient temperature for 24 hr and filtered. The filtrate was washed with water until neutral and the organic layer was dried over anhydrous $MgSO_4$ and evaporated. The oily product was transformed to the corresponding oxalate by addition of an ethereal solution of oxalic acid to the solution of the compound in ether. A white solid product was obtained by scratching the ethereal solution and keeping it in a refrigerator overnight.

The white solid was isolated by filtration and thoroughly washed with ether and dried to give 0.7 gm (23%). $R_f$ ($CHCl_3$: MeOH 3:1)=0.23, m.p. 112°–115° C.

| Anal. for $C_{17}H_{21}O_4N.(COOH)_2.0.5H_2O$ | | | |
|---|---|---|---|
| | C % | H % | N % |
| Theoretical | 56.71 | 6.01 | 3.48 |
| Found | 56.94 | 6.26 | 3.32 |

According to microanalytical and NMR data, the compound obtained has the following structure:

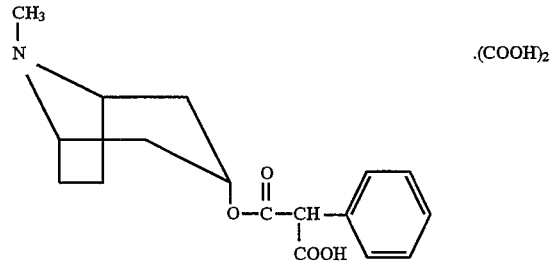

EXAMPLE 7

Preparation of (±)-8-Methyl-8-azabicyclo[3.2.1]oct-3-yl (α-Cyclohexyloxycarbonyl-α-phenyl)acetate Methiodide A solution of (±)-8-methyl-8-azabicyclo[3.2.1]oct-3-yl (α-cyclohexyloxycarbonyl-α-phenyl)acetate (3.85 g, 0.01 mol) and 10 mL of methyl iodide in 30 mL of dry benzene was stirred at room temperature for 6 hr. The mixture was filtered and the solid was dried and recrystallized from methanol-ether mixture to give a yellowish-white product.

$R_f$: 0.35 Yield: 55.9% M.p.: 228°–230° C.

| Anal. for $C_{24}H_{34}INO_4 \cdot 0.25\ H_2O$ | | | |
|---|---|---|---|
| | C % | H % | N % |
| Theoretical | 54.19 | 6.53 | 2.63 |
| Found | 54.00 | 6.48 | 2.50 |

Based on microanalytical and NMR data, the obtained compound has the following structure:

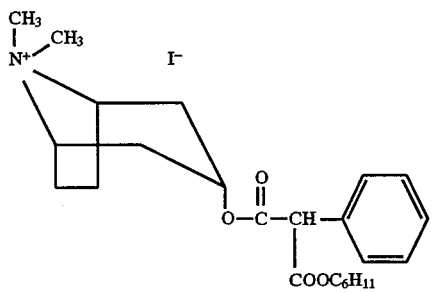

EXAMPLE 8

Preparation of (±)-8-Methyl-8-azabicyclo[3.2.1]oct-3-yl (α-Ethoxycarbonyl-α-phenyl)acetate Methiodide A solution of (±)-8-methyl-8-azabicyclo[3.2.1]oct-3-yl (α-ethoxycarbonyl-α-phenyl)acetate (3.31 g, 0.01 mol) and 10 mL of methyl iodide in 25 mL of dry benzene was stirred at room temperature for 6 hr. The mixture was filtered and the solid was dried and recrystallized from an alcohol-ether mixture.

$R_f$: 0.41 M.p.: 232°–234° C. (dec.).

| Anal. for $C_{20}H_{28}INO_4$ | | | |
|---|---|---|---|
| | C % | H % | N % |
| Theoretical | 50.75 | 5.92 | 2.96 |
| Found | 50.55 | 5.97 | 2.97 |

According to microanalytical and NMR data, the compound has the following structure:

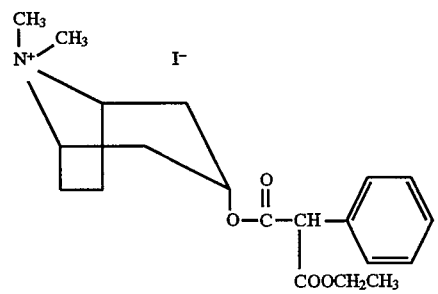

EXAMPLE 9

Preparation of (±)-8-Methyl-8-azabicyclo[3.2.1]oct-3-yl (α-Methoxycarbonyl-α-phenyl)acetate Dimethylsulfate A solution of (±)-8-methyl-8-azabicyclo[3.2.1]oct-3-yl (α-methoxycarbonyl-α-phenyl)acetate in dry ethyl ether and dimethylsulfate (2× moles of the ester), was stirred at room temperature overnight. The white solid was filtered, dried, and recrystallized from methanol-ether.

M.p.: 138°–140° C.

| Anal. for $C_{20}H_{29}NO_8S \cdot 1/2\ H_2O$ | | | | |
|---|---|---|---|---|
| | C % | H % | N % | S % |
| Theoretical | 53.08 | 6.68 | 3.09 | 7.08 |
| Found | 53.06 | 6.65 | 3.01 | 7.14 |

According to microanalytical and NMR data, the compound has the following structure:

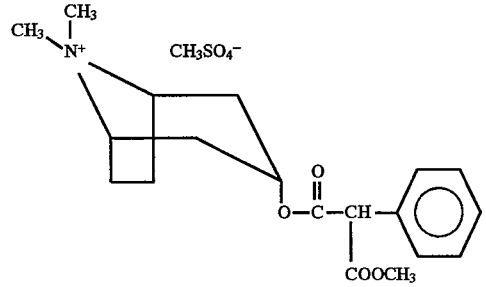

EXAMPLE 10

Preparation of (±)-8-Methyl-8-azabicyclo[3.2.1]oct-3-yl (α-Ethoxycarbonyl-α-phenyl)acetate Dimethylsulfate A solution of (±)-8-methyl-8-azabicyclo[3.2.1]oct-3-yl (α-ethoxycarbonyl-α-phenyl)acetate in dry ethyl ether and dimethylsulfate (2× moles of the ester) was stirred at room temperature overnight. The white solid was filtered, dried and recrystallized from methanol-ether.

M.p.: 165°–167° C.

| Anal. for $C_{21}H_{31}NO_8S$ | | | | |
|---|---|---|---|---|
| | C % | H % | N % | S % |
| Theoretical | 55.13 | 6.83 | 3.06 | 7.01 |
| Found | 55.10 | 6.87 | 2.96 | 7.02 |

Based on microanalytical and NMR data, the compound has the following structure:

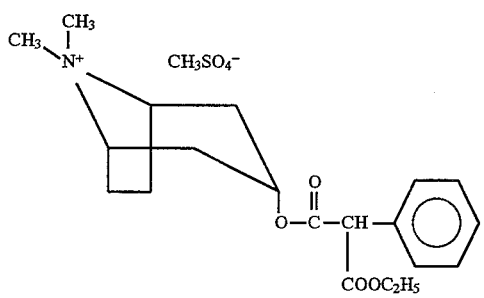

EXAMPLE 11

Preparation of (±)-8-Methyl-8-azabicyclo[3.2.1]oct-3-yl (α-Isopropoxycarbonyl-α-phenyl)acetate Dimethylsulfate A solution of (±)-8-methyl-8-azabicyclo[3.2.1]oct-3-yl (α-isopropoxycarbonyl-α-phenyl)acetate in dry ethyl ether and dimethylsulfate (2× moles of the ester) was stirred at room temperature overnight. The white solid was filtered, dried and recrystallized from methanol-ether.

M.p.: 128°–130° C.

| Anal. for $C_{22}H_{33}NO_8S$ | | | | |
|---|---|---|---|---|
| | C % | H % | N % | S % |
| Theoretical | 56.03 | 7.05 | 2.97 | 6.80 |
| Found | 55.91 | 7.08 | 2.96 | 6.78 |

According to microanalytical and NMR data, the compound has the following structure:

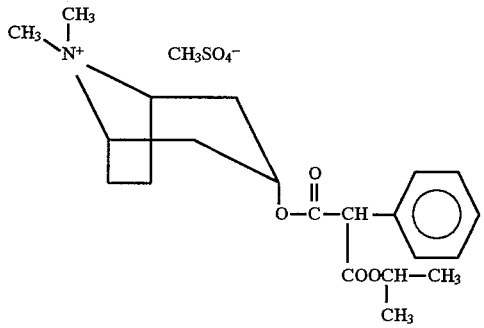

EXAMPLE 12

Preparation of (±)-8-Methyl-8-azabicyclo[3.2.1]oct-3-yl (α-Cyclohexyloxycarbonyl-α-phenyl)acetate Dimethylsulfate A solution of (±)-8-methyl-8-azabicyclo[3.2.1]oct-3-yl (α-cyclohexyloxycarbonyl-α-phenyl)acetate in dry ethyl ether and dimethylsulfate (2× moles of the ester) was stirred at room temperature overnight. The white solid was filtered, dried, and recrystallized from methanol-ether.

M.p.: 196°–198° C.

| Anal. for $C_{25}H_{37}NO_8S \cdot 1/2\ H_2O$ | | | | |
|---|---|---|---|---|
| | C % | H % | N % | S % |
| Theoretical | 57.67 | 7.36 | 2.69 | 6.16 |
| Found | 57.91 | 7.15 | 2.68 | 6.17 |

According to microanalytical and NMR data, the compound has the following structure:

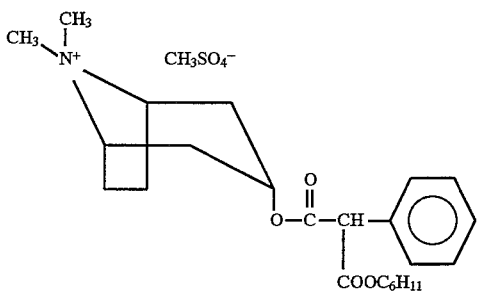

In the examples which follow, compounds which were tested are numbered as follows:

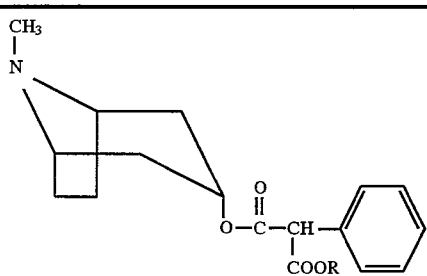

| Compound No. | R | |
|---|---|---|
| 1 | —$CH_3$ | |
| 2 | —$CH_2CH_3$ | |
| 3 | —$CH(CH_3)_2$ | |
| 4 | —cyclohexyl | |
| 5 | —$CH_2CH_3$ | (methiodide salt) |
| 6 | —cyclohexyl | (methiodide salt) |
| 7 | H | |

EXAMPLE 13

Kinetic Studies of the New Tropanyl Esters

A high pressure liquid chromatography (HPLC) method was used for the determination of rates of hydrolysis of the newly prepared tropanyl esters in aqueous buffered solution at pH 12.0 and in human plasma.

The chromatographic analysis was performed in a system consisting of LCD/Milton Roy Consta Metric III metering pump and LCD UV III Monitor Detector operated at 254 nm. A 30 cm×3.9 mm (internal diameter) reverse phase ASI/U Bondpak C18 column operated at ambient temperature was used for the analysis. The mobile phase consisted of 32% acetonitrile in 0.01M potassium dihydrogen phosphate, 0.004M 1-octanesulfonic acid sodium salt in 0.1% acetic acid at a flow rate of 2.3 mL/min.

Determination of the Hydrolytic Rate Constants in Aqueous Buffered Solution at pH 12 at 37° C.

Sodium hydroxide and sodium dibasic phosphate were used to prepare the buffer at pH 12. The ionic strength was maintained at 0.1M with sodium chloride.

One hundred microLiters of a freshly prepared solution of the compound in methanol was added to 10 mL buffered solution, previously equilibrated to 37° C. in a water bath and mixed thoroughly to make an initial concentration of $6×10^{-3}$ mol. Liter$^{-1}$. Samples of 100 µL were injected into the column at various time intervals. The rate constants, half-lives and standard errors were calculated and the results are listed in Table 1. The following retention times at a flow rate of 2.3 mL/min. using 32% acetonitrile are:

Compound (1) had a retention time of 3.0 minutes.
Compound (2) had a retention time of 7.3 minutes.
Compound (3) had a retention time of 9.3 minutes.
Compound (5) had a retention time of 4.7 minutes.
Compound (7) had a retention time of 3.5 minutes.

At a flow rate of 2.0 mL/min, compound 7 had a retention time of 4.0 min. A mobile phase of 40% acetonitrile was used to separate compounds 4 and 6 at a flow rate of 2.0 mL/min.

Compound (4) had a retention time of 8.0 minutes.
Compound (6) had a retention time of 6.6 minutes.

TABLE 1

Compound (5)

$K±S.E.(min^{-1})=80.8±0.75×10^{-2}$ t ½ (min)=0.85.

The kinetic studies for the hydrolysis of the new tropines in aqueous buffer solution at pH 12.0 and in human plasma was carried out using HPLC method.

EXAMPLE 14

Determination of the Hydrolytic Rate Constants in Aqueous Buffer at pH 12.0

The previous method adapted for the hydrolysis of compounds 1, 2, 3 and 5 was used for the determination of rate of hydrolysis of compounds 4, 6 and 7. In case of compounds 4 and 6, the mobile phase was 40% acetonitrile, 0.01M KH$_2$PO$_4$, 0.04M 1-octanesulfonic acid sodium salt and 0.1% acetic acid, at a flow rate 2 mL/min. Compounds 4 and 6 had retention time of 8.0 and 6.6 min, respectively, as shown in Table 2. Compound 7 had a retention time of 3.1 min at a flow rate of 2.3 mL/min and 3.5 min at 2.0 mL/min.

TABLE 2

The observed First Order Hydrolytic Rate Constants (K), the standard error (S.E.) and half-life (t ½) in 0.01 N sodium hydroxide at pH 12.0, at 37° C.

| Compound No. | R | K$^a$ ± S.E. (min$^{-1}$) | t ½ (min) |
|---|---|---|---|
| 1 | —CH$_3$ | 1.43 ± 0.12 × 10$^{-1}$ | 4.80 |
| 2 | —CH$_2$—CH$_3$ | 16.9 ± 0.15 × 10$^{-2}$ | 4.08 |
| 3 | —CH(CH$_3$)$_2$ | 30 ± 0.77 × 10$^{-3}$ | 22.81 |

$^a$Average of three runs ± S.E.M.

The observed pseudo first order hydrolytic rate constants (K) and half lives (t ½) on 0.01 M sodium hydroxide at pH 12 and 37° C.

| Compound No. | R | K (min$^{-1}$)$^a$ S.E.M. | t ½ (min) |
|---|---|---|---|
| 4 | cyclohexyl | 379 ± 0.8 × 10$^{-5}$ | 182 |
| 6$^b$ | cyclohexyl | 5.43 ± 0.1 × 10$^{-1}$ | 1.28 |
| 7 | H | 19.8 ± 0.3 × 10$^{-4}$ | 350 |

$^a$Average of three runs.
$^b$The quaternary iodide salt of the ester 4.

EXAMPLE 15

Determination of the Enzymatic Hydrolytic Cleavage Rates in Human Plasma at 37° C.

Freshly collected plasma was used which contained about 80% plasma diluted with anticoagulant citrate phosphate dextrose solution, U.S.P.

A 100 µL volume of a freshly prepared solution of the compound in methanol was added to 10 mL plasma, previously equilibrated at 37° C. in a water bath, and mixed thoroughly to result in an initial concentration of $6\times10^{-3}$ mol. Liter$^{-1}$. One mL samples of plasma were withdrawn from the test medium, mixed immediately with 3 mL ice cold acetonitrile, centrifuged and the supernatant analyzed by HPLC. The first order hydrolytic rate constant was determined by following the disappearance of the compound as a function of time. The results are given in Table 3.

TABLE 3

The observed first order hydrolytic rate constants (K) and half lives (t ½) in human plasma at 37° C.

| Compound No. | R | K (min$^{-1}$) ± S.E.M. | t ½ (hr) |
|---|---|---|---|
| 2 | —CH$_2$CH$_3$[a] | $15.0 \pm 0.3 \times 10^{-5}$ | 77.4 |
| 3 | —CH(CH$_3$)$_2$ | $6.27 \pm 0.3 \times 10^{-5}$ | 185.5 |
| 4 | 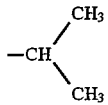 | $4.44 \pm 0.4 \times 10^{-5}$ | 269.8 |
| 5 | —CH$_2$CH$_3$[b] | $14.1 \pm 0.6 \times 10^{-5}$ | 82.2 |
| 6 | 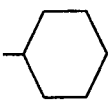[c] | $6.31 \pm 0.8 \times 10^{-5}$ | 183.2 |

[a]Average of 4 runs, the rest of data are average of 3 runs.
[b]The quaternary iodide salt of the ester 2.
[c]The quaternary iodide salt of the ester 4.

EXAMPLE 16

Determination of the Rate of Hydrolysis of Tertiary Ethyl Ester (2) and Rate of Formation of its Degradation Product (7) in 0.01M NaOH at pH 12 and 37° C.

The mobile phase used for the separation of compound (2) and its degradation product, the half ester (7), consisted of 32% CH$_3$CN, 0.01M KH$_2$PO$_4$, 0.004M 1-octanesulfonic acid sodium salt and 0.1% acetic acid. At a flow rate of 1.5 mL/min, (2) and (7) have retention times of 9 min and 4.6 min, respectively.

Procedure 100 microLiters of a freshly prepared solution of compound (2) in methanol was added to 10 mL buffered solution (pH 12), previously equilibrated to 37° C. in a water bath to result in an initial concentration of $6\times10^{-3}$ mol Liter$^{-1}$. Samples of 1 mL were taken at time intervals and mixed with 3 mL of acetonitrile. 100 microLiters of the collected samples were injected and disappearance of (2) and formation of (7) was followed by HPLC.

The results are given in Table 4.

TABLE 4

Rate of hydrolysis of tertiary ethyl ester (2) to the half ester (7) in 0.01 N NaOH, pH at 37° C.

| Compound No. | K$_{obsd}$(min$^{-1}$) ± S.E.M. | t 1/2 (min) |
|---|---|---|
| 2 | $16.5 \pm 0.58 \times 10^{-2}$ | $4.19 \pm 0.14$ |
| 7 | $1.68 \pm 0.34 \times 10^{-1}$ | $3.79 \pm 0.66$ |

EXAMPLE 17

Rate of Hydrolysis of Tropanyl Hydrogen Phenyl Malonate (7) to the Dibasic Acid (Phenylmalonic Acid) in 0.01N Sodium Hydroxide, pH 12 at 37° C.

The previously described method for the determination of rate of hydrolysis of compound (2) was followed for the determination of hydrolysis of compound (7).

The disappearance of compound (7) was followed by HPLC.

The concentration of the formed dibasic acid was determined by HPLC. 15% acetonitrile, 0.01M KH$_2$PO$_4$ and 0.1% acetic acid were used as a mobile phase. At a flow rate of 2 mL/min, the product has a retention time of 4 min.

The collected samples, after determination of rate of disappearance of compound (7), were used for the determination of rate of formation of the hydrolysis product (8). 100 microLiters of the sample was injected and the formation of the product was followed by HPLC.

The results are given in Table 5.

TABLE 5

| Compound No. | K$_{obsd}$(min$^{-1}$) ± S.E.M. | t 1/2 (min) |
|---|---|---|
| 7 | $20.9 \pm 0.27 \times 10^{-4}$ | $331.25 \pm 4.31$ |
| 8 | $21.7 \pm 0.95 \times 10^{-4}$ | $316.01 \pm 33.5$ |

EXAMPLE 18

Determination of the Enzymatic Hydrolysis of the New Esters in Rat Liver Homogenate at 37° C.

The liver homogenate was prepared by the following method. Two Sprague-Dawley rats were killed by decapitation and the livers were removed, weighed and homogenized in a tissue homogenizer in 0.11M aqueous phosphate buffer, pH 7.4, to make 20% liver homogenate. The homogenate was centrifuged and the supernatant was used for the test. 100 µL of 0.6M solution of the ester in methanol was mixed with 10 mL of the homogenate, previously equilibrated to 37° C. in a water bath, to result in an initial concentration of $6\times10^{-3}$ mol. Liter$^{-1}$. Samples of 1.0 mL were withdrawn at time intervals from the medium, added immediately to 3 mL ice-cold acetonitrile, shaken vigorously, and placed in a freezer. When all samples had been collected, they were centrifuged and each supernatant was analyzed by HPLC.

The results are shown in Table 6.

TABLE 6

Rates of hydrolysis in liver homogenate of selected tropanyl esters.

| Compound No. | R | K (min$^{-1}$) ± S.E. | t ½ (min) |
|---|---|---|---|
| 2 | —CH$_2$CH$_3$[a] | 1.99 ± 0.996 × 10$^{-1}$ | 3.48 |
| 3 | —CH(CH$_3$)$_2$ | 97.2 ± 0.76 × 10$^{-3}$ | 7.12 |
| 4 | cyclohexyl[c] | 35.0 ± 0.3 × 10$^{-3}$ | 18.73 |
| 5 | —CH$_2$CH$_3$[b] | 10.5 ± 0.28 × 10$^{-2}$ | 6.6 |
| 6 | cyclohexyl[c] | 10.4 ± 0.23 × 10$^{-3}$ | 66.8 |

[a]Mobile phase used for Compounds 2, 3 and 5 was 32% acetonitrile, 0.01 M KH$_2$PO$_4$, 0.004 M 1-octane sulfonic acid sodium salt and 0.1% acetic acid. Mobile phase used for compounds 4 and 6 was 40% acetonitrile, 0.01 M KH$_2$PO$_4$, 0.004 M 1-octane-sulfonic acid sodium salt and 0.1% acetic acid.
[b]It is the methiodide of Compound 2.
[c]It is the methiodide of Compound 4.

EXAMPLE 19

Pharmaceutical Study of the New Tropanyl Esters

The anticholinergic activity of all the new compounds was investigated in vitro by studying the inhibitory action of the drugs on carbachol-induced spasms of strips of ileum from freshly killed guinea pigs. The terminal ileum from guinea pig (200–500 g) was cut into 2–3 cm strips and suspended in freshly prepared Tyrode's solution in 40 mL organ bath. The solution was aerated with 95% oxygen and 5% carbon dioxide at 37° C. A tension of 1 g was applied to the tissue, and cumulative-response curves were recorded with carbachol until constant responses were obtained. A concentration of the antagonist was then added to the bath and after 10 seconds, further concentration response curves to carbachol were established. This procedure was then repeated using increasing concentrations of the antagonist. EC$_{50}$ was calculated for carbachol alone and for carbachol in the presence of the various antagonist concentrations. PA$_2$ value for each tested compound is listed in Table 7. Atropine was used as a standard for comparison. The PA$_2$ was calculated as follows:

$$PA_2 = \log (A/a-1) - \log [\text{antagonist}]$$

A=EC$_{50}$ or carbachol in presence of the antagonist a=EC$_{50}$ for carbachol alone before adding antagonist

TABLE 7

| Compound No.[a] | R | PA$_2$ |
|---|---|---|
| Atropine | | 8.29 |
| 1 | —CH$_3$ | 6.55[b] |
| 2 | —CH$_2$CH$_3$ | 6.72 |
| 3 | —CH(CH$_3$)$_2$ | 7.55 |
| 4 | cyclohexyl | 6.59[b] |
| 5[c] | —CH$_2$CH$_3$ | 7.86 |
| 6[d] | cyclohexyl | 7.35 |
| 7 | H | 6.20 |

[a]Results were the average of two experiments, except as otherwise noted.
[b]Average of three experiments.
[c]Quaternary iodide salt of tertiary ethyl ester.
[d]Quaternary iodide salt of cyclohexyl ester.

EXAMPLE 20

Synthesis of (±)-8-Methyl-8-azabicyclo[3.2.1]oct-3-yl (α-Isopropoxycarbonyl-α-phenyl)acetate Methiodide

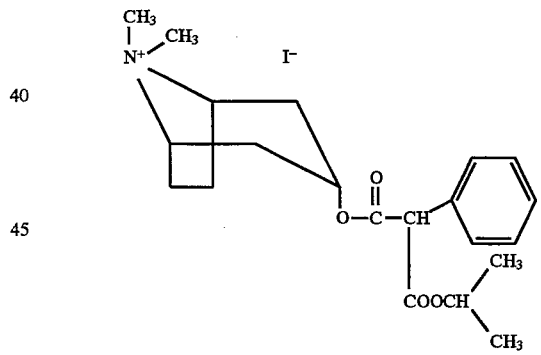

To a solution of 2.07 g (0.006 mol) of (±)-8-methyl-8-azabicyclo[3.2.1]oct-3-yl (α-isopropoxycarbonyl-α-phenyl) acetate in 20 mL of dry benzene was added 6 mL methyl iodide and the mixture was stirred at room temperature for 6 hr. The yellowish white solid product was filtered, dried and crystallized from ethanol-ether mixture to yield 1.8 g (61.56%) of the title compound, m.p. 251°–254° C.

| Anal. for C$_{21}$H$_{30}$INO$_4$.0.5 H$_2$O. | | | |
|---|---|---|---|
| | C % | H % | N % |
| Theoretical | 50.81 | 6.29 | 2.82 |
| Found | 50.67 | 6.25 | 2.95 |

The pharmacological result: PA$_2$=7.61.

EXAMPLE 21

The mydriatic activity of the compounds is illustrated by the following procedure.

The mydriatic activity of the soft ester drug (Compound 5) was evaluated in 0.9% saline solution at concentrations of 0.05% and 0.1% compared to 0.1% tropicamide (Mydriacyl®). Normal New Zealand albino rabbits of either sex weighing about 2 kg were employed. The animals were placed in wooden restraining boxes. Standard doses of 50 µL were applied to the rabbits' eyes and pupillary changes were measured in a light and temperature controlled room. The degree of pupil dilation, in millimeters, was measured with a Starrett micrometer held at a constant distance at time intervals of 15, 30, 60, 90, 120, 180, 240, 300 and 360 minutes. The differences in the same animals between the pupil diameter of the eye with drug versus the other eye with saline was recorded. Each point on the graph is the average obtained on 3–6 animals. The recovery time is defined as that time required for the pupil diameter to return to 1.0 millimeter in diameter.

The results are set forth in FIG. 1 which depicts mydriasis as a function of time. Tropicamide is typical of the shortest acting of the commercially available anticholinergic mydriatic agents. The active agent therein is tropicamide—chemical name=Benzeneacetamide N-ethyl-α-(hydroxymethyl)-N-(4-pyridinylmethyl)—. As is apparent from the results depicted in FIG. 1, the "recovery time", i.e., recovery from mydriasis, is much shorter with the compositions and methods of the invention than with the commercially available products.

Tables 8, 9 and 10 below set forth yield and analysis data for compounds depicted therein prepared according to the above-described procedures. Table 11 below sets forth hydrolysis kinetic data in various media for several compounds according to the invention. Table 12 below sets forth anticholinergic activities for various of the compounds according to the present invention. See Table 11 for the identities of the compounds identified by Roman numerals. The activities were determined according to the method described in Example 19.

TABLE 8

OXALATE SALTS OF SOFT ANTICHOLINERGIC AGENTS

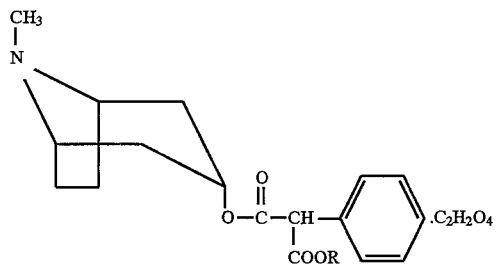

| Compound | R | m.p.[a] °C. | Yield % | Formula | Calculated C % | H % | N % | Found C % | H % | N % |
|---|---|---|---|---|---|---|---|---|---|---|
| II | H | 112–115 | 23 | $C_{17}H_{21}NO_4 \cdot C_2H_2O_4 \cdot 0.5H_2O$ | 56.71 | 6.01 | 3.48 | 56.94 | 6.26 | 3.32 |
| Va | $CH_3$ | 89–91 | 64.5 | $C_{18}H_{23}NO_4 \cdot C_2H_2O_4 \cdot H_2O$ | 56.47 | 6.39 | 3.29 | 56.48 | 6.2 | 2.94 |
| Vb | $CH_2CH_3$ | 135–137 | 75 | $C_{19}H_{25}NO_4 \cdot C_2H_2O_4$ | 59.85 | 6.45 | 3.32 | 59.88 | 6.52 | 3.3 |
| Vc | $CH(CH_3)_2$ | 78–80 | 72.4 | $C_{20}H_{27}NO_4 \cdot C_2H_2O_4$ | 60.68 | 6.71 | 3.21 | 60.41 | 6.77 | 3.13 |
| Vd | $C_6H_{11}$ | 160–162 | 77.91 | $C_{23}H_{31}NO_4 \cdot C_2H_2O_4$ | 63.15 | 6.99 | 2.94 | 63.05 | 7.26 | 2.78 |

[a]All compounds were recrystallized from methanol-ether.

TABLE 9
QUATERNARY IODIDES

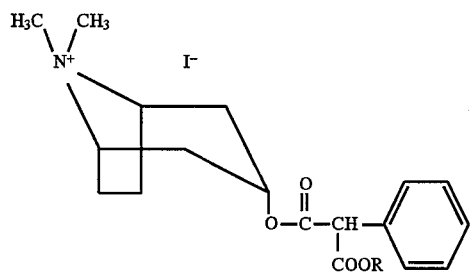

| Compound | R | m.p. °C. | Cryst. Solvent | Yield % | Formula | Calculated C | H | N | Found C | H | N |
|---|---|---|---|---|---|---|---|---|---|---|---|
| VIb | —CH₂CH₃ | 232–234 (dec) | methanol-ether | 50.9 | C₂₀H₂₈INO₄ | 50.75 | 5.92 | 2.96 | 50.55 | 5.97 | 2.97 |
| VIc | —CH(CH₃)₂ | 251–254 | ethanol-ether | 61.56 | C₂₁H₃₀INO₄ · 0.5H₂O | 50.81 | 6.29 | 2.82 | 50.67 | 6.26 | 2.95 |
| VId | C₆H₁₁ | 228–230 | methanol-ether | 55.9 | C₂₄H₃₄INO₄ · 0.25H₂O | 54.19 | 6.53 | 2.63 | 54.00 | 6.48 | 2.50 |

TABLE 10
QUATERNARY DIMETHYLSULFATES

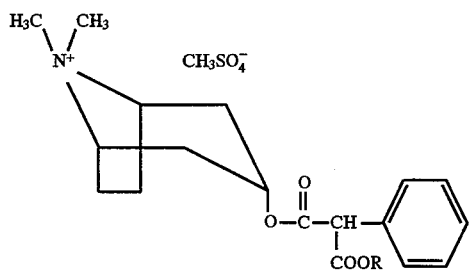

| Compound | R | m.p. °C. | Cryst. Solvent | Yield % | formula | Calculated C | H | N | S | Found C | H | N | S |
|---|---|---|---|---|---|---|---|---|---|---|---|---|---|
| VIIa | CH₃ | 138–140 | Methanol/Ether | 22 | C₂₀H₂₉NO₈S·H₂O | 53.08 | 6.68 | 3.09 | 7.08 | 53.06 | 6.65 | 3.01 | 7.14 |
| VIIb | C₂H₅ | 165–167 | Methanol/Ether | 62 | C₂₁H₃₁NO₈S | 55.13 | 6.83 | 3.06 | 7.01 | 55.10 | 6.87 | 2.96 | 7.02 |
| VIIc | CH(CH₃)₂ | 128–130 | Methanol/Ether | 48 | C₂₂H₃₃NO₈S | 56.03 | 7.05 | 2.97 | 6.80 | 55.91 | 7.08 | 2.96 | 6.78 |
| VIId | C₆H₁₁ | 196–198 | Methanol/Ether | 36 | C₂₅H₃₇NO₈S·½H₂O | 57.67 | 7.36 | 2.69 | 6.16 | 57.91 | 7.15 | 2.68 | 6.17 |

TABLE 11

HYDROLYSIS KINETICS IN AQUEOUS SOLUTION (pH 12), HUMAN PLASMA (37° C.) AND RAT LIVER HOMOGENATE (37° C.)

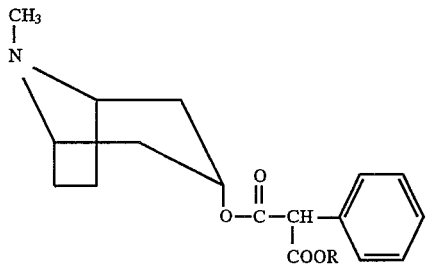

| Compound | R | t ½ (Min) Aqueous Soln, pH 12[a], 37° C. ($k_{obsd}$ min$^{-1}$) | t ½ (h) Human Plasma, 37° C[a] ($k_{obsd}$ min$^{-1}$) | t ½ (Min) Rat Liver Homogenate, 37° C.[a] ($k_{obsd}$ min$^{-1}$) |
|---|---|---|---|---|
| II | H | 350 (19.8 ± 0.3 × 10$^{-4}$) | — | — |
| Va | Me | 4.80 (1.43 ± 0.12 × 10$^{-1}$) | — | — |
| Vb | Et | 4.08 (16.9 ± 0.15 × 10$^{-2}$) | 77.4 (15.0 ± 0.3 × 10$^{-5}$) | 3.48 (1.99 ± 0.996 × 10$^{-1}$) |
| Vc | i-Pr | 22.8 (30 ± 0.77 × 10$^{-3}$) | 185.5 (6.27 ± 0.3 × 10$^{-5}$) | 7.12 (97.2 ± 0.76 × 10$^{-3}$) |
| Vd | c-Hexyl | 182 (379 ± 0.8 × 10$^{-5}$) | 269.8 (4.44 ± 0.4 × 10$^{-5}$) | 18.7 (37.0 ± 0.3 × 10$^{-3}$) |
| VIb | Et (N$^+$)[b] | 0.85 (80.8 ± 0.75 × 10$^{-2}$) | 82.2 (14.1 ± 0.6 × 10$^{-5}$) | 6.6 (10.5 ± 0.28 × 10$^{-2}$) |
| VId | c-Hexyl (H$^+$)[b] | 1.28 (5.43 ± 0.1 × 10$^{-1}$) | 183.2 (6.31 ± 0.8 × 10$^{-5}$) | 66.8 (10.4 ± 0.23 × 10$^{-3}$) |

[a]Average of three runs ± SEM.
[b]Tests were performed with the quaternary methiodide salts.

TABLE 12

ANTICHOLINERGIC ACTIVITY OF SOFT ATROPINE AGENTS

| SOFT DRUG R | PA$_2$ TERTIARY AMINE | PA$_2$ QUATERNARY AMINE[a] |
|---|---|---|
| H | 6.20 (II) | — |
| Me | 6.55 (Va) | — |
| Et | 6.72 (Vb) | 7.85 (VIb) |
| i-Pr | 7.55 (Vc) | 7.61 (VIc) |
| c-Hexyl | 6.59 (Vd) | 7.35 (VId) |
| Atropine | 8.29 | — |

[a]Tests were carried out with the quaternary methiodide soft esters.

EXAMPLE 22

The antiperspirant/antisecretory activity of the compounds of the invention illustrated by the following procedure.

Forearm Antiperspirant Test

Ref.: F. S. K. MacMillan, H. H. Reller and F. H. Snyder, J. Investig. Dermatol., 43, 363–377 (1964); R. B. Stoughton, F. Chiu, W. Fritsch, and D. Nurse, ibid 42, 151–155 (1964).

Circles, 4.5 cm$^2$ in area, were marked on the inner aspect of the forearm about ¾ inch apart. The antiperspirant solution was applied with a cotton-tipped swab and allowed to dry. This was done three times for each area. A total of 0.1–0.2 mL was applied in this manner. After an appropriate time interval, often about 5 hours, the forearm was washed with soap and water and rinsed thoroughly to remove any excess of the material and the areas were treated with 3% iodine in alcohol until the skin was an orange/yellow color when dry, then covered with a fine slurry of 50% starch in castor oil. Subjects were placed in a room at 88°–94° F. and a relative humidity of 70–80%. Degree of inhibition of sweating was determined after 30 minutes.

The ethyl and cyclohexyl soft diester analogs of atropine (the quaternary salts, Compounds 5 and 6) showed inhibition of eccrine sweat glands using this method and serve as soft drug examples of antiperspirant activity (Tables A and B). The soft agents are designed to be less toxic than atropine, scopolamine and other anticholinergic, antisecretory agents if absorbed into the systemic circulation due to their chemical and/or enzymatic deactivation to an inactive metabolite. Passage of any intact molecules across the blood-brain barrier into the central nervous system and their resultant toxic effects would also be prevented when the quaternary ammonium feature is incorporated in the soft antisecretory molecular structure.

EXAMPLE 23

The general procedure of Example 2 is repeated, except that the ethanol reactant employed in step (a) is replaced with an equivalent quantity of a different alcohol reactant, as specified below. Atropine soft drugs of the formula

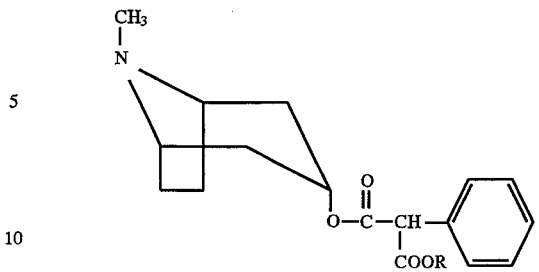

are thus obtained.

| Alcohol Reactant for Step (a) | R in Product |
|---|---|
| n-butanol | —CH$_2$CH$_2$CH$_2$CH$_3$ |
| 2-cyclohexylethanol | —CH$_2$CH$_2$—⬡ |
| cyclohexylmethanol | —CH$_2$—⬡ |
| 2,6-dimethylcyclohexanol | H$_3$C—⬡—CH$_3$ |
| 1-adamantanemethanol | —CH$_2$—adamantyl |
| 1-adamantaneethanol | —CH$_2$CH$_2$—adamantyl |
| 2-norbornanemethanol | norbornyl—CH$_2$— |
| cholesterol | cholesteryl |
| n-propanol | —CH$_2$CH$_2$CH$_3$ |
| n-pentanol | —(CH$_2$)$_4$CH$_3$ |
| n-hexanol | —(CH$_2$)$_5$CH$_3$ |
| n-heptanol | —(CH$_2$)$_6$CH$_3$ |
| n-octanol | —(CH$_2$)$_7$CH$_3$ |

-continued

| Alcohol Reactant for Step (a) | R in Product |
|---|---|
| 3,5-dimethylcyclohexanol | 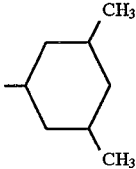 |
| 4-methylcyclohexanol | 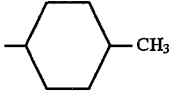 |
| 4-tert-butylcyclohexanol | 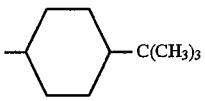 |
| epiandrosterone | 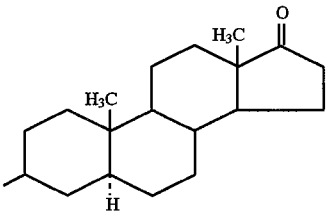 |
| isopinocampheol | 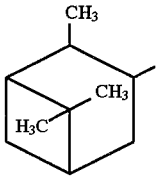 |
| endo-norborneol | 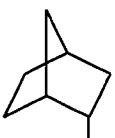 |
| exo-norborneol | 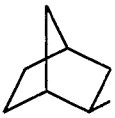 |
| (1S)-endo-(–)-borneol | 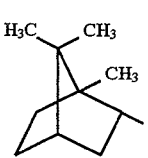 |

When these products are quaternized according to the process of Examples 8 and 9, the corresponding methiodides and dimethylsulfates, respectively, are obtained.

EXAMPLE 24

The general procedure of Example 2 is repeated, except that the ethanol reactant utilized in step (a) is replaced with an equivalent quantity of the alcohol reactant specified below, and the tropine reactant employed in step (c) is replaced with an equivalent quantity of 6,7-epoxytropine (scopine). Scopolamine soft drugs of the formula

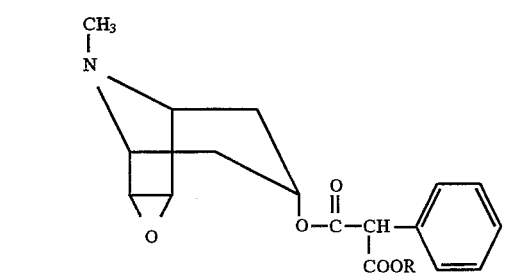

are thus obtained.

| Alcohol Reactant for Step (a) | R in Product |
|---|---|
| n-butanol | —CH$_2$CH$_2$CH$_2$CH$_3$ |
| 2-cyclohexylethanol | —CH$_2$CH$_2$—  |
| cyclohexylmethanol | —CH$_2$—  |
| 2,6-dimethylcyclohexanol | 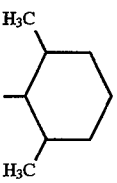 |
| 1-adamantanemethanol | —CH$_2$— 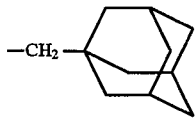 |
| 1-adamantaneethanol | —CH$_2$CH$_2$— 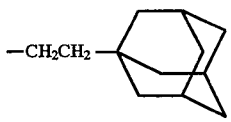 |
| 2-norbornanemethanol | 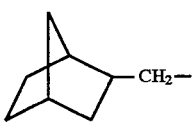—CH$_2$— |
| cholesterol | 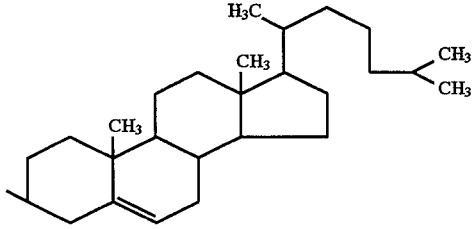 |
| cyclohexanol | 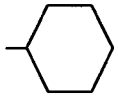 |
| ethanol | —CH$_2$CH$_3$ |
| isopropanol | —CH(CH$_3$)$_2$ |
| methanol | —CH$_3$ |
| n-propanol | —CH$_2$CH$_2$CH$_3$ |
| n-pentanol | —(CH$_2$)$_4$CH$_3$ |
| n-hexanol | —(CH$_2$)$_5$CH$_3$ |
| n-heptanol | —(CH$_2$)$_6$CH$_3$ |
| n-octanol | —(CH$_2$)$_7$CH$_3$ |
| 3,5-dimethylcyclohexanol | 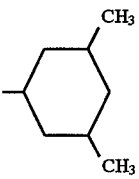 |

| Alcohol Reactant for Step (a) | R in Product |
|---|---|
| 4-methylcyclohexanol | ![cyclohexyl-CH3] |
| 4-tert-butylcyclohexanol | ![cyclohexyl-C(CH3)3] |
| epiandrosterone | ![steroid structure] |
| isopinocampheol | ![isopinocampheyl] |
| endo-norborneol | ![endo-norbornyl] |
| exo-norborneol | ![exo-norbornyl] |
| (1S)-endo-(−)-borneol | ![bornyl] |

When these products are quaternized according to the process of Examples 8 and 9, the corresponding methiodides and dimethylsulfates, respectively, are obtained.

EXAMPLE 25

When the general procedure of Example 2 is followed, substituting an equivalent quantity of the alcohol reactant specified below in place of the ethanol reactant employed in step (a) and substituting an equivalent quantity of N-ethyl-N-(4-pyridylmethyl)amine for the tropine reactant employed in step (c), tropicamide soft drugs of the formula

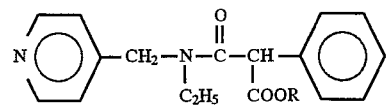

are obtained.

| Alcohol Reactant for Step (a) | R in Product |
|---|---|
| n-butanol | —CH$_2$CH$_2$CH$_2$CH$_3$ |
| 2-cyclohexylethanol | —CH$_2$CH$_2$—cyclohexyl |

-continued

| Alcohol Reactant for Step (a) | R in Product |
|---|---|
| cyclohexylmethanol | —CH₂—(cyclohexyl) |
| 2,6-dimethylcyclohexanol | 2,6-dimethylcyclohexyl (H₃C, H₃C substituents) |
| 1-adamantanemethanol | —CH₂—(1-adamantyl) |
| 1-adamantaneethanol | —CH₂CH₂—(1-adamantyl) |
| 2-norbornanemethanol | (2-norbornyl)—CH₂— |
| cholesterol | cholesteryl group |
| cyclohexanol | cyclohexyl |
| ethanol | —CH₂CH₃ |
| isopropanol | —CH(CH₃)₂ |
| methanol | —CH₃ |
| n-propanol | —CH₂CH₂CH₃ |
| n-pentanol | —(CH₂)₄CH₃ |
| n-hexanol | —(CH₂)₅CH₃ |
| n-heptanol | —(CH₂)₆CH₃ |
| n-octanol | —(CH₂)₇CH₃ |
| 3,5-dimethylcyclohexanol | 3,5-dimethylcyclohexyl |
| 4-methylcyclohexanol | 4-methylcyclohexyl (—CH₃) |
| 4-tert-butylcyclohexanol | 4-tert-butylcyclohexyl —C(CH₃)₃ |

| Alcohol Reactant for Step (a) | R in Product |
|---|---|
| epiandrosterone | 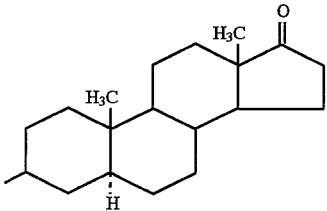 |
| isopinocampheol | 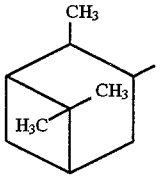 |
| endo-norborneol |  |
| exo-norborneol |  |
| (1S)-endo-(−)-borneol | 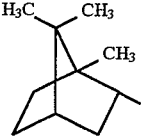 |

When these products are quaternized according to the process of Examples 8 and 9, the corresponding methiodides and dimethylsulfates, respectively, are obtained.

EXAMPLE 26 d, l or l-Phenylsuccinic anhydride (0.1 mol) is dissolved in benzene (30–50 fold), and a solution of 0.1 mol of alcohol or amine reactant as specified below in an equal volume of benzene is introduced gradually, with stirring. In the case of the amine reactant, 0.1 mol of triethylamine is included as an acid scavenger. At the end of the addition, the reaction mixture is warmed to gentle reflux and maintained at that temperature for 1 hour. The reaction mixture is washed twice with water, then with 5% aqueous sodium bicarbonate solution until neutral, then twice more with water. The solvent is evaporated and the crude monoester or amide thus obtained is then reacted with thionyl chloride according to the general procedure of Example 2 (b) to afford the monoester acid chloride or amide acid chloride, which is then esterified with an alcohol $R^1OH$ as specified below according to the procedure of Example 2 (c) to afford the corresponding oxalate salts of the free bases shown below.

Using tropine as the alcohol reactant in the first step:

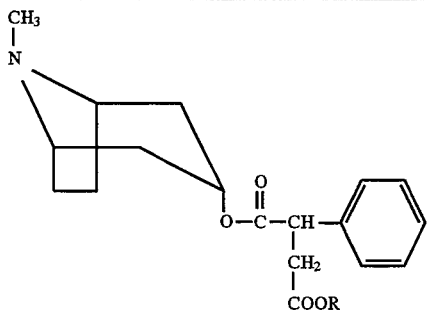
| Alcohol reactant in final step | R in product |
|---|---|
| n-butanol | —CH$_2$CH$_2$CH$_2$CH$_3$ |
| 2-cyclohexylethanol | 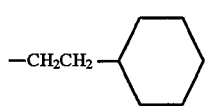 |
| cyclohexylmethanol | 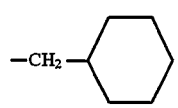 |
| 2,6-dimethylcyclohexanol | 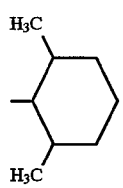 |
| 1-adamantanemethanol | 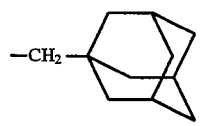 |
| 1-adamantaneethanol | 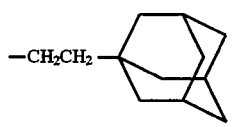 |
| 2-norbornanemethanol | 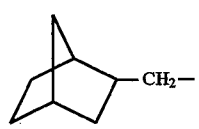 |
| cholesterol | 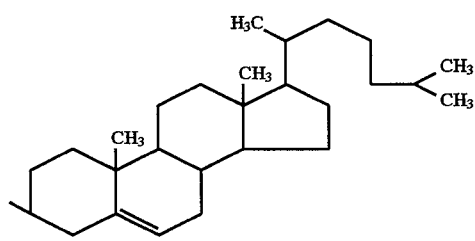 |
| cyclohexanol | 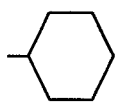 |
| ethanol | —CH$_2$CH$_3$ |
| isopropanol | —CH(CH$_3$)$_2$ |
| methanol | —CH$_3$ |
| n-propanol | —CH$_2$CH$_2$CH$_3$ |
| n-pentanol | —(CH$_2$)$_4$CH$_3$ |
| n-hexanol | —(CH$_2$)$_5$CH$_3$ |

-continued
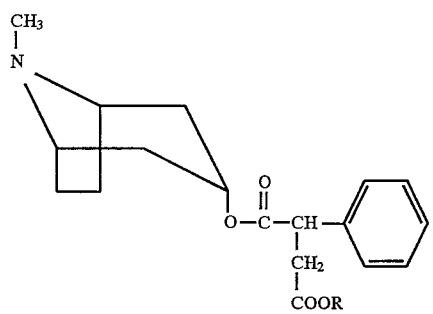
| Alcohol reactant in final step | R in product |
|---|---|
| n-heptanol | —$(CH_2)_6CH_3$ |
| n-octanol | —$(CH_2)_7CH_3$ |
| 3,5-dimethylcyclohexanol | 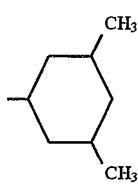 |
| 4-methylcyclohexanol | 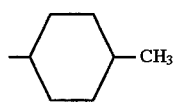 |
| 4-tert-butylcyclohexanol | 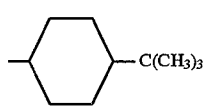 |
| epiandrosterone | 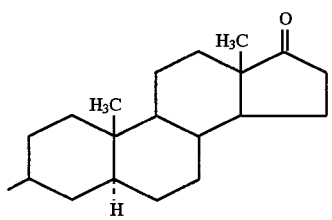 |
| isopinocampheol | 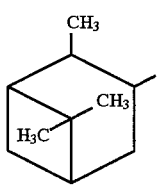 |
| endo-norborneol |  |
| exo-norborneol | 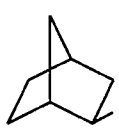 |

-continued
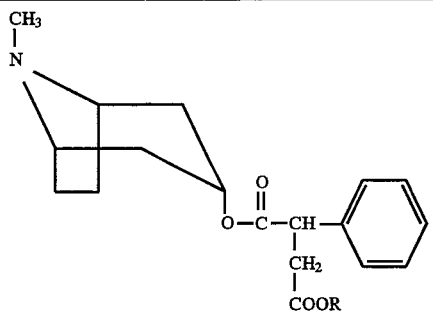
| Alcohol reactant in final step | R in product |
|---|---|
| (1S)-endo-(−)-borneol | 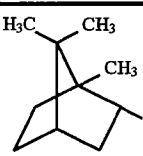 |
Using scopine as the alcohol reactant in the first step:
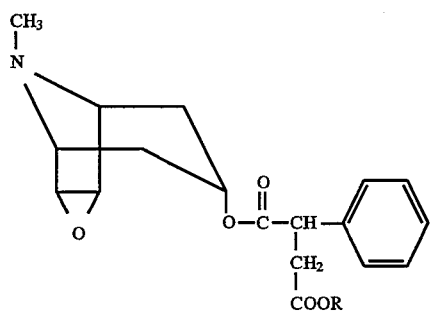
| Alcohol reactant in final step | R in product |
|---|---|
| n-butanol | —CH$_2$CH$_2$CH$_2$CH$_3$ |
| 2-cyclohexylethanol | 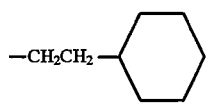 |
| cyclohexylmethanol | 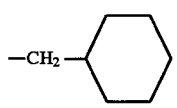 |
| 2,6-dimethylcyclohexanol | 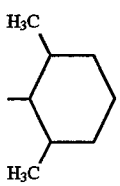 |
| 1-adamantanemethanol | 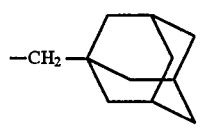 |

-continued

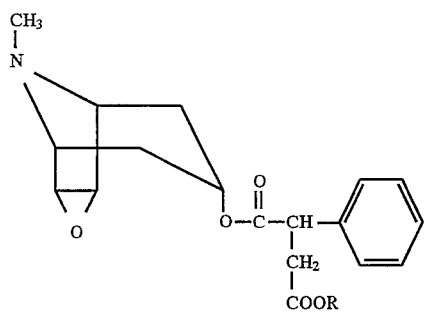

| Alcohol reactant in final step | R in product |
|---|---|
| 1-adamantaneethanol | 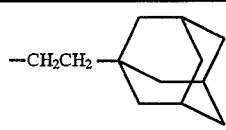 —CH₂CH₂— |
| 2-norbornanemethanol | 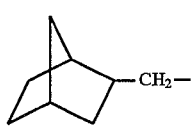 —CH₂— |
| cholesterol | 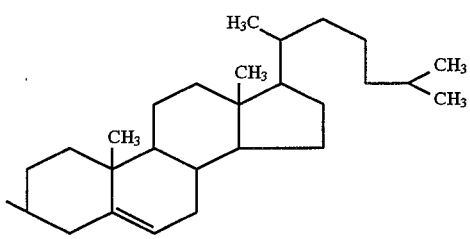 |
| cyclohexanol | 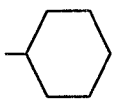 |
| ethanol | —CH₂CH₃ |
| isopropanol | —CH(CH₃)₂ |
| methanol | —CH₃ |
| n-propanol | —CH₂CH₂CH₃ |
| n-pentanol | —(CH₂)₄CH₃ |
| n-hexanol | —(CH₂)₅CH₃ |
| n-heptanol | —(CH₂)₆CH₃ |
| n-octanol | —(CH₂)₇CH₃ |
| 3,5-dimethylcyclohexanol | 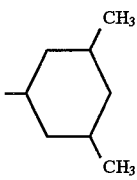 |
| 4-methylcyclohexanol | 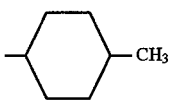 —CH₃ |
| 4-tert-butylcyclohexanol | 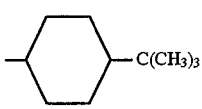 —C(CH₃)₃ |

-continued
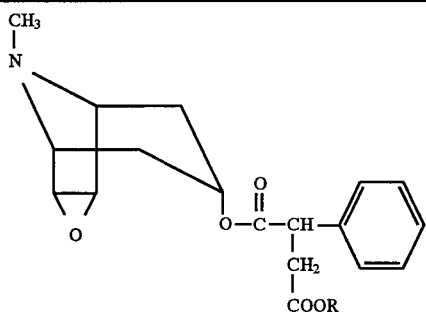
| Alcohol reactant in final step | R in product |
|---|---|
| epiandrosterone | 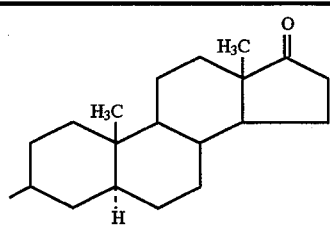 |
| isopinocampheol | 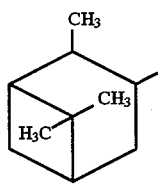 |
| endo-norborneol | 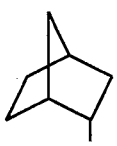 |
| exo-norborneol |  |
| (1S)-endo-(−)-borneol | 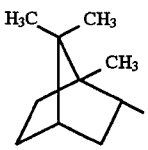 |
Using N-ethyl-N-(4-pyridylmethyl)amine as the amine reactant in the first step:

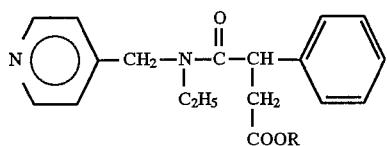

| Alcohol reactant in final step | R in product |
|---|---|
| n-butanol | —CH$_2$CH$_2$CH$_2$CH$_3$ |
| 2-cyclohexylethanol | —CH$_2$CH$_2$—[cyclohexyl] |
| cyclohexylmethanol | —CH$_2$—[cyclohexyl] |
| 2,6-dimethylcyclohexanol | [2,6-dimethylcyclohexyl] |
| 1-adamantanemethanol | —CH$_2$—[adamantyl] |
| 1-adamantaneethanol | —CH$_2$CH$_2$—[adamantyl] |
| 2-norbornanemethanol | [norbornyl]—CH$_2$— |
| cholesterol | [cholesteryl] |
| cyclohexanol | [cyclohexyl] |
| ethanol | —CH$_2$CH$_3$ |
| isopropanol | —CH(CH$_3$)$_2$ |
| methanol | —CH$_3$ |
| n-propanol | —CH$_2$CH$_2$CH$_3$ |
| n-pentanol | —(CH$_2$)$_4$CH$_3$ |
| n-hexanol | —(CH$_2$)$_5$CH$_3$ |
| n-heptanol | —(CH$_2$)$_6$CH$_3$ |
| n-octanol | —(CH$_2$)$_7$CH$_3$ |

-continued

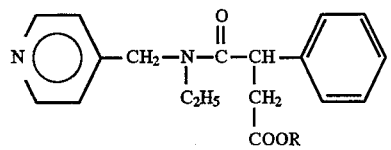

| Alcohol reactant in final step | R in product |
|---|---|
| 3,5-dimethylcyclohexanol | 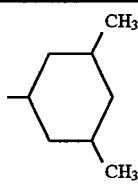 |
| 4-methylcyclohexanol | 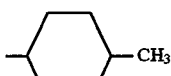 |
| 4-tert-butylcyclohexanol | 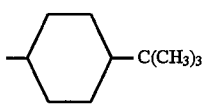 |
| epiandrosterone | 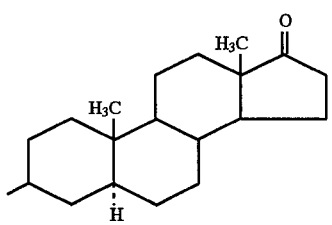 |
| isopinocampheol | 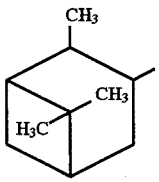 |
| endo-norborneol | 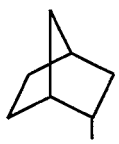 |
| exo-norborneol |  |
| (1S)-endo-(–)-borneol | 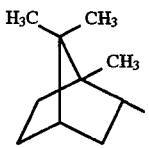 |

When the products of this Example are quaternized according to the process of Examples 8 and 9, the corresponding methiodides and dimethylsulfates, respectively, are obtained.

For therapeutic use as an anticholinergic agent or as a mydriatic agent, a compound of formula (I) or its acid addition or quaternary ammonium salt can be conveniently administered in the form of a pharmaceutical composition containing the formula (I) compound or its salt and a pharmaceutically acceptable carrier therefor. Suitable carriers vary with the desired form of the pharmaceutical composition and may include diluents or excipients such as fillers, binders, wetting agents, disintegrators, surface-active agents, lubricants and the like.

The compound of the invention or its salt, in an effective anticholinergic or mydriasis-inducing amount, may be formulated together with the carrier into any desired unit dosage form, the dosage form of choice depending upon the ultimate use of the selected compound. Typical unit dosage forms include tablets, pills, powders, solutions, suspensions, emulsions, gels, ointments, granules, capsules and suppositories.

In the preparation of tablets, carriers which are widely used in this field can be employed, e.g. excipients such as lactose, sucrose, sodium chloride, glucose solution, urea, starch, calcium carbonate, kaolin, crystalline cellulose and silicic acid; binding agents such as water, ethanol, propanol, simple syrup, glucose, starch solution, gelatin solution, carboxymethyl cellulose, shellac, methyl cellulose, calcium phosphate and polyvinylpyrrolidone; disintegrators such as dried starch, sodium alginate, agar-agar powder, laminalia powder, sodium bicarbonate, calcium carbonate, Tweens, sodium lauryl sulfate, stearic acid monoglyceride, starch and lactose; disintegration inhibitors such as sucrose, stearin, coconut butter and hydrogenated oil; absorption accelerators such as quaternary ammonium bases and sodium lauryl sulfate; wetting agents such as glycerin and starch; adsorbing agents such as starch, lactose, kaolin, bentonite and colloidal silicic acid; and lubricants such as purified talc, stearic acid salts, boric acid powder, Macrogol and solid polyethylene glycol.

In the preparation of pills, carriers which are known and widely used in this field can also be used, for example, excipients such as glucose, lactose, starch, coconut butter, hydrogenated vegetable oils, kaolin and talc; binders such as powdered gum arabic, powdered tragacanth, gelatin and ethanol; and disintegrators such as laminaria and agar-agar. In the case of tablets, they can be further coated with the usual coating materials to make sugar-coated tablets, gelatin film-coated tablets, tablets coated with enteric coatings, tablets coated with films or double-layered tablets and multi-layered tablets.

In order to form suppositories, carriers which are known and widely used in this field can also be used, for example, polyethylene glycols, coconut butter, higher alcohols, esters of higher alcohols, gelatin and semi-synthesized glycerides.

Furthermore, the usual dissolving agents, buffers, analgesic agents and preservatives can be added, as well as coloring materials, perfumes, seasoning agents, sweetening agents and other medicines, to the pharmaceutical compositions, if necessary or if desired.

The amount of a compound of formula (I) or its salt to be present in the pharmaceutical composition can be suitably be selected from a wide range, but usually 1 to 70% by weight of the total composition is preferable when the composition is a solid dosage form.

As to the route of administration, same will vary with the particular composition used. For example, tablets, pills, solutions, suspensions, emulsions, granules and capsules can be administered orally; suppositories can be administered rectally.

The dosage of the compound of the present invention or its salt and frequency of administration is selected according to the usage, purpose and conditions of symptoms, as well as the size and species of the recipient. For example, when the compound or salt is administered therapeutically as an anticholinergic, usually 0.006 mg to 6.0 mg per kg of body weight per day will suffice.

The compounds of the present invention and their acid addition and quaternary ammonium salts induce mydriasis when applied topically/locally to the eye, thus are of particular use in dilating the pupils during ophthalmic examinations, for eye surgery and in the treatment of certain eye conditions. The instant compounds and their salts can be conveniently administered for these purposes by formulating the selected compound or salt, in an effective mydriasis-inducing amount, together with a non-toxic ophthalmically acceptable carrier therefor. Suitable carriers will be apparent to those skilled in the art of ophthalmic formulations. Obviously, the choice of suitable carriers will depend on the exact nature of the particular dosage form desired, e.g. whether the soft mydriatic agent of the invention is to be formulated into an ophthalmic solution or suspension (typically for use as eye drops), an ophthalmic ointment or cream or an ophthalmic gel. Preferred dosage forms are solutions, which contain a major amount of water in addition to the active ingredient. Minor amounts of other ingredients such as pH adjusters (e.g. a base such as NaOH), emulsifiers or dispersing agents, buffering agents, preservatives, wetting agents and jelling agents (e.g. methylcellulose) may also be present. Most preferably, the ophthalmic composition is a sterile, isotonic, buffered aqueous solution. Generally speaking, the ophthalmic composition containing the instant mydriatic may be prepared and may contain the various inert ingredients or carriers as previously described in the patent or non-patent literature as being suitable for ophthalmic compositions comprising known anticholinergic-type mydriatic agents such as tropine, scopolamine, homatropine and the like. The amount of the soft mydriatic of this invention which will be present in the ophthalmic composition will of course vary with the particular soft mydriatic employed and the type of formulation selected. Generally speaking, the composition will contain 0.01 to 5% of a compound of formula (I), preferably 0.25 to 2.5%; in other words, each mL of solution will contain 0.1 to 50 mg, preferably 2.5 to 25 mg, of the free base. The dose administered ophthalmically will be selected according to the particular compound employed, the size and condition of the patient and the effect desired, but in any event will be a quantity sufficient to cause mydriasis. To dilate the pupils for ophthalmic examination, 1 or 2 drops per eye of the solution will generally suffice.

Similarly, in a typical topical formulation for topical application as an antiperspirant, any one of the compounds or salts of the instant invention can be combined with any suitable topical vehicle safe for underarm application. The vehicle may be solid, liquid or aerosol. Vehicles serving the aforementioned purpose are readily found in *Remington's Pharmaceutical Sciences* (Fourteenth Edition) 1970 and the text entitled, *Cosmetics, Science and Technology*, H. D. Goulden, et al, Interscience Publishers (1957), pp. 5, 717–31, 826–9, 1016, 1211, 1255 and 1266, respectively. When topically administered to inhibit perspiration, a 0.01% to 25% by weight composition applied in the usual manner will normally be sufficient. Generally speaking, a usual application would consist of approximately 1 mL of a lotion composition (e.g. a roll-on formulation) or 1 gram of a dry (e.g. stick) composition, applied daily.

From the foregoing description, one of ordinary skill in the art can easily ascertain the essential characteristics of the instant invention, and without departing from the spirit and scope thereof, can make various changes and/or modifications of same to adapt it to various usages and conditions. Consequently, these changes and/or modifications are properly, equitably and intended to be, within the full range of equivalence of the following claims.

What we claim is:

1. A compound of the formula

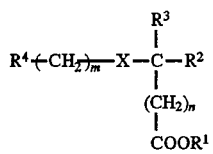

wherein:

$R^1$ is $C_1$–$C_8$ straight or branched alkyl; $C_2$–$C_8$ straight or branched alkenyl; ($C_3$–$C_8$ cycloalkyl)-$C_pH_{2p}$— wherein p is an integer from 0 to 4, and wherein the 3- to 8-membered ring portion optionally bears 1 to 4 $C_1$–$C_4$ straight or branched alkyl substituents; ($C_3$–$C_8$ cycloalkenyl)-$C_pH_{2p}$— wherein p is an integer from 0 to 4 and wherein the 3- to 8-membered ring portion optionally bears 1 to 4 $C_1$–$C_4$ straight or branched alkyl substituents; $C_6H_5$—$C_qH_{2q}$— wherein q is an integer from 1 to 4; or ($C_6$–$C_{18}$ polycarbocyclic)-$C_pH_{2p}$— wherein p is an integer from 0 to 4, the 6- to 18-membered ring portion consisting of 2 to 4 rings which are bridged or fused, which are saturated or unsaturated and which optionally bear one or more $C_1$–$C_8$ straight or branched alkyl substituents, the total carbon atom content of all such optional alkyl substituents being from 1 to 10;

$R^2$ is phenyl optionally bearing 1 to 3 $C_1$–$C_4$ straight or branched alkyl substituents; $C_3$–$C_8$ branched alkyl; $C_3$–$C_8$ branched alkenyl; ($C_3$–$C_8$ cycloalkyl)-$C_pH_{2p}$— wherein p is an integer from 0 to 4, and wherein the 3- to 8-membered ring portion optionally bears 1 to 4 $C_1$–$C_4$ straight or branched alkyl substituents; ($C_3$–$C_8$ cycloalkenyl)-$C_pH_{2p}$— wherein p is an integer from 0 to 4 and wherein the 3- to 8 -membered ring portion optionally bears 1 to 4 $C_1$–$C_4$ straight or branched alkyl substituents; $C_6H_5$—$C_qH_{2q}$— wherein q is an integer from 1 to 4; or ($C_6$–$C_{18}$ polycarbocyclic)-$C_pH_{2p}$— wherein p is an integer from 0 to 4, the 6- to 18-membered ring portion consisting of 2 to 4 rings which are bridged or fused, which are saturated or unsaturated and which optionally bear one or more $C_1$–$C_8$ straight or branched alkyl substituents, the total carbon atom content of all such optional alkyl substituents being from 1 to 10;

$R^3$ is H, phenyl optionally bearing 1 to 3 $C_1$–$C_4$ straight or branched alkyl substituents, $C_1$–$C_8$ straight or branched alkyl or ($C_3$–$C_8$ cycloalkyl)-$C_pH_{2p}$— wherein p is an integer from 0 to 4 and wherein the 3- to 8-membered ring portion optionally bears 1 to 4 $C_1$–$C_4$ straight or branched alkyl substituents;

n is an integer from 0 to 4;

X is

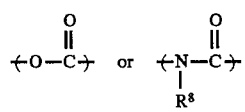

wherein $R^8$ is H or $C_1$–$C_5$ straight or branched alkyl; m is an integer from 0 to 4;

and $R^4$ is a piperidinyl ring, optionally bearing 1 or 2 substituents selected from the group consisting of methyl, phenyl and benzyl;

or a pharmaceutically acceptable acid addition salt of a compound of formula (I) with an acid of the formula HY wherein Y is a pharmaceutically acceptable anion;

or a pharmaceutically acceptable quaternary ammonium salt of a compound of formula (I) with a compound of the formula $R^{12}Y$ wherein Y is defined as above and $R^{12}$ is $C_1$–$C_4$ straight or branched alkyl or benzyl.

2. The compound or salt according to claim 1, wherein $R^1$ is ($C_3$–$C_8$ cycloalkyl)-$C_pH_{2p}$—.

3. The compound or salt according to claim 2, wherein p is 0.

4. The compound or salt according to claim 2, wherein p is 1 or 2.

5. The compound or salt according to claim 2, wherein $R^1$ is cyclohexyl, 2-cyclohexylethyl, cyclohexylmethyl, 2,6-dimethylcyclohexyl, 3,5-dimethylcyclohexyl, 4-methylcyclohexyl or 4-tert-butylcyclohexyl.

6. The compound or salt according to claim 1, wherein $R^1$ is $C_1$–$C_8$ straight or branched alkyl.

7. The compound or salt according to claim 6, wherein $R^1$ is methyl, ethyl, n-propyl, isopropyl, n-butyl, n-pentyl, n-hexyl, n-heptyl or n-octyl.

8. The compound or salt according to claim 1, wherein $R^1$ is ($C_6$–$C_{18}$ polycarbocyclic)-$C_pH_{2p}$—.

9. The compound or salt according to claim 8, wherein $R^1$ is 1-adamantylmethyl, 1-adamantylethyl, 2-norbornylethyl, isopinocamphyl, endo-norbornyl, exo-norbornyl or (1S)-endo-bornyl.

10. The compound or salt according to claim 1, wherein $R^2$ is phenyl.

11. The compound or salt according to claim 1, wherein n is 0.

12. The compound or salt according to claim 1, wherein n is 1.

13. The compound or salt according to claim 1, wherein $R^3$ is H.

14. The compound or salt according to claim 1, wherein X is

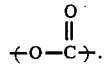

15. The compound or salt according to claim 1, wherein X is

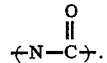

16. The compound or salt according to claim 1, wherein m is 0.

17. The quaternary ammonium salt according to claim 1, wherein $R^{12}$ is —$CH_3$ and Y is halide, sulfate, alkylsulfate or alkylsulfonate.

18. The quaternary ammonium salt according to claim 17, wherein Y is halide or methylsulfate.

19. The compound according to claim 1, having the formula

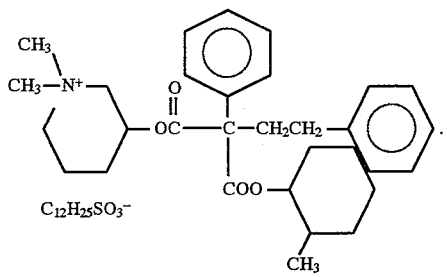

20. An ophthalmic composition of matter, in unit dosage form, comprising a mydriatically effective amount of a compound or salt as claimed in claim 1 and an ophthalmically acceptable carrier therefor.

21. A topical antiperspirant composition of matter comprising an effective antisecretory amount of a compound or salt as claimed in claim 1 and a topically acceptable carrier therefor.

22. A method for eliciting mydriasis in a warm-blooded animal in need of same, said method comprising administering to the eye or eyes of said animal a mydriatically effective amount of a compound or salt as claimed in claim 1.

23. A method for eliciting an antiperspirant response in a warm-blooded animal in need of same, said method comprising topically administering to the skin of said animal an effective antisecretory amount of a compound or salt as claimed in claim 1.

* * * * *